United States Patent [19]

Nesvadba

[11] Patent Number: 5,428,162
[45] Date of Patent: Jun. 27, 1995

[54] 3-(2-ACYLOXYETHOXYPHENYL)BEN-ZOFURAN-2-ONES FOR USE AS STABILIZERS

[75] Inventor: Peter Nesvadba, Marly, Switzerland

[73] Assignee: Ciba-Geigy Corporation, Ardsley, N.Y.

[21] Appl. No.: 124,139

[22] Filed: Sep. 20, 1993

[30] Foreign Application Priority Data

Sep. 23, 1992 [CH] Switzerland .......................... 2979/92

[51] Int. Cl.$^6$ ................. C07D 307/28; C07D 251/30; C07C 59/68
[52] U.S. Cl. ...................... 544/221; 549/60; 549/222; 549/305; 562/470; 562/426; 562/444
[58] Field of Search .......... 562/470, 426, 444; 549/305, 60, 222; 544/180, 221

[56] References Cited

U.S. PATENT DOCUMENTS

| | | | |
|---|---|---|---|
| 4,325,863 | 4/1982 | Hinsken et al. | 624/111 |
| 4,338,244 | 7/1982 | Hinsken et al. | 524/109 |
| 4,426,380 | 1/1984 | Weak et al. | 424/244 |
| 5,175,312 | 12/1992 | Dubs et al. | 549/307 |

FOREIGN PATENT DOCUMENTS

| | | |
|---|---|---|
| 0182507 | 10/1985 | European Pat. Off. . |
| 0397170 | 11/1990 | European Pat. Off. . |
| 2944295 | 5/1980 | Germany . |
| 4202276 | 8/1992 | Germany . |
| 2034308 | 6/1980 | United Kingdom . |
| 2257140 | 1/1993 | United Kingdom . |
| 2257141 | 1/1993 | United Kingdom . |
| WO8001566 | 8/1980 | WIPO . |

OTHER PUBLICATIONS

Bradley et al., J. Chem. Soc. 1956, 1622–1627.
J. Mowan et al., Bull. Soc. Chim. Fr. 1979, II-575-582.
M. Auger, et al., Bull. Soc. Chim, Fr. 1970, 4024–4030.
Organikum 1986, 402–408.
Houben-Weyl, Methoden der Organischen Chemie, vol. 6/1C, 1030 (1976).
Acta Chemica Scand. 23, 2583–2588 (1969).
M. H. Hubacher J. Org. Chem. 24, (1959) 1949–1951.

Primary Examiner—C. Warren Ivy
Assistant Examiner—A. A. Owens
Attorney, Agent, or Firm—Luther A. R. Hall

[57] ABSTRACT

Novel compounds of the formula (1),

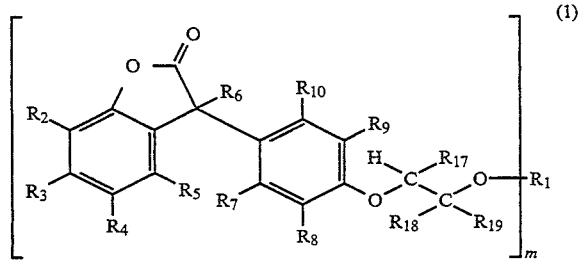

in which $R_1$ is hydrogen or acyl, $R_2$ to $R_5$ are independently hydrogen, chloro, alkyl phenylalkyl, aryl, cycloalkyl, alkoxy, alkylthio, hydroxy, amino or substituted amino, $R_6$ is hydrogen, $R_7$ to $R_{10}$ are independently hydrogen, alkyl or alkoxy, $R_{17}$ or $R_{19}$ is hydrogen or alkyl, and $R_{18}$ is hydrogen, alkyl, aralkyl or aryl, are described for use as stabilizers for organic materials against thermal, oxidative or light-induced degradation.

14 Claims, No Drawings

3-(2-ACYLOXYETHOXYPHENYL)BENZOFURAN-2-ONES FOR USE AS STABILIZERS

The present invention relates to novel 3-(2-acyloxyethoxyphenyl)benzofuran-2-ones, compositions comprising an organic material, preferably a polymer, and the novel stabilizers, and to the use of same for stabilizing organic materials against oxidative, thermal or light-induced degradation.

Individual 3-(hydroxyphenyl)benzofuran-2-ones and 3-(acetoxyphenyl)benzofuran-2-ones have been described, for example by M. H. Hubacher, J. Org. Chem. 24, 1949 (1959); J. Gripenberg et al, Acta Chemica Scandinavica 23, 2583 (1969); M. Auger et al, Bull. Soc. Chim. Fr. 1970, 4024 and J. Morvan et al, Bull. Soc. Chim. Fr. 1979, II-575.

The use of some benzofuran-2-ones as stabilizers for organic polymers is disclosed, for example, in U.S. Pat. Nos. 4,325,863; 4,338,244 and EP-A-415 887.

It has now been found that a selected group of such benzofuran-2-ones are particularly suitable for use as stabilizers for organic materials which are sensitive to oxidative, thermal or light-induced degradation.

Accordingly, the present invention provides compounds of the formula (1),

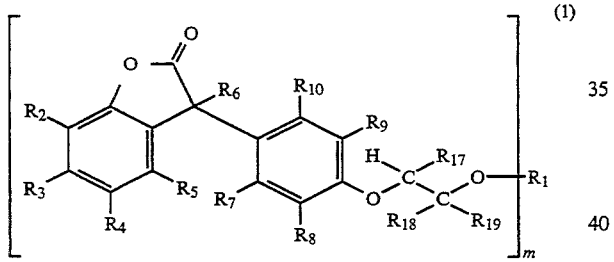

in which, if m is 1, $R_1$ is hydrogen, $C_1$–$C_{25}$alkanoyl, $C_3$–$C_{25}$alkenoyl, $C_3$–$C_{25}$alkanoyl which is interrupted by oxygen, sulfur or

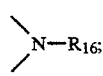

$C_2$–$C_{25}$alkanoyl substituted by a di($C_1$–$C_6$alkyl)-phosphonate group; $C_6$–$C_9$cycloalkylcarbonyl, thenoyl, furoyl, benzoyl or $C_1$–$C_{12}$alkyl-substituted benzoyl;

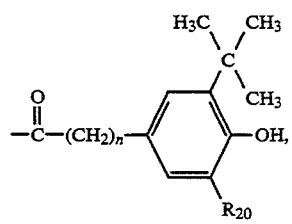

-continued

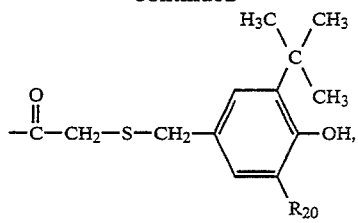

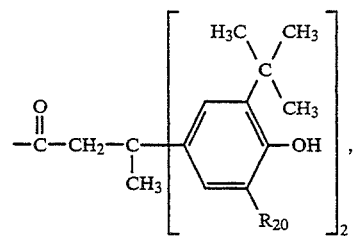

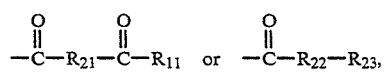

and,
if m is 2,

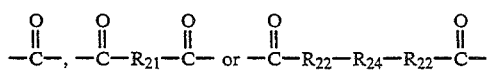

and,
if m is 3,
$R_1$ is $C_4$–$C_{18}$alkanetricarbonyl, $C_9$–$C_{18}$aryltricarbonyl,

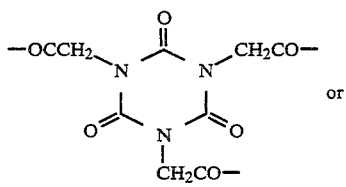

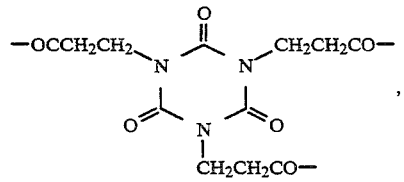

and,
m is 4,
$R_1$ is $C_6$–$C_{18}$alkanetetracarbonyl or $C_{10}$–$C_{18}$aryltetracarbonyl, $R_2$, $R_3$, $R_4$ and $R_5$, independently of one another, are hydrogen, chlorine, $C_1$–$C_{25}$alkyl, $C_7$–$C_9$phenylalkyl, unsubstituted or $C_1$–$C_4$alkyl-substituted phenyl, unsubstituted or $C_1$–$C_4$-alkyl-substituted $C_5$–$C_9$cycloalkyl; $C_1$–$C_{18}$alkoxy, $C_1$–$C_{18}$alkylthio, hydroxyl, $C_1$–$C_4$alkylamino, di($C_1$–$C_4$-alkyl)amino, $C_1$–$C_{25}$alkanoyloxy, $C_1$–$C_{25}$alkanoylamino, $C_3$–$C_{25}$alkenoyloxy, $C_3$–$C_{25}$alkanoyloxy which is interrupted by oxygen, sulfur or:

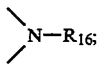

$C_6$–$C_9$cycloalkylcarbonyloxy, benzoyloxy or $C_1$–$C_{12}$alkyl-substituted benzoyloxy, or, furthermore, the radicals $R_2$ and $R_3$ or the radicals $R_3$ and $R_4$ or the radicals $R_4$ and $R_5$ together with the carbon atoms to which they are attached form a phenyl ring, $R_4$ is additionally —$(CH_2)_n$—$COR_{11}$, or, if $R_3$, $R_5$, $R_6$, $R_7$ and $R_{10}$ are hydrogen, $R_4$ is additionally a radical of the formula (2)

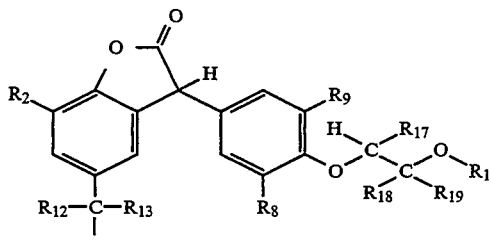

(2)

in which $R_1$ is as defined above for m=1,
$R_6$ is hydrogen or a radical of the formula (3)

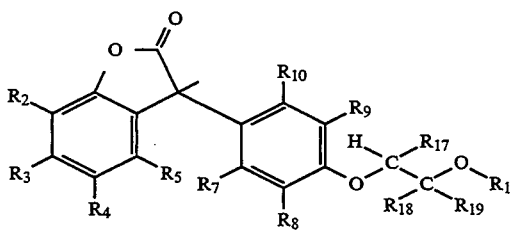

(3)

in which $R_4$ is not a radical of the formula (2) and $R_1$ is as defined above for m=1,
$R_7$, $R_8$, $R_9$ and $R_{10}$, independently of one another, are hydrogen, $C_1$–$C_4$alkyl or $C_1$–$C_4$alkoxy, on the condition that at least one of the radicals $R_7$, $R_8$, $R_9$ and $R_{10}$ is hydrogen,
$R_{11}$ is hydroxyl,

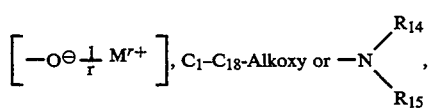, $C_1$–$C_{18}$-Alkoxy or $R_{12}$ and $R_{13}$, independently of one another, are hydrogen, $CF_3$, $C_1$–$C_{12}$ alkyl or phenyl, or
$R_{12}$ and $R_{13}$ together with the carbon atom to which they are attached form a $C_5$–$C_8$cycloalkylidene ring which is unsubstituted or substituted by 1 to 3 $C_1$–$C_4$alkyl groups;
$R_{14}$ and $R_{15}$, independently of one another, are hydrogen or $C_1$–$C_4$alkyl,
$R_{16}$ is hydrogen or $C_1$–$C_4$alkyl,
$R_{17}$ is hydrogen or $C_1$–$C_4$alkyl,
$R_{18}$ is hydrogen, unsubstituted or $C_1$–$C_4$alkyl-substituted phenyl; $C_1$–$C_{25}$alkyl, $C_2$–$C_{25}$alkyl which is interrupted by oxygen, sulfur or

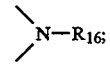

$C_7$–$C_9$phenylalkyl which is unsubstituted or substituted on the phenyl radical by 1 to 3 $C_1$–$C_4$alkyl groups; $C_7$–$C_{25}$phenylalkyl which is interrupted by oxygen, sulfur or

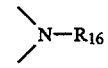

and unsubstituted or substituted on the phenyl radical by 1 to 3 $C_1$–$C_4$alkyl groups, or, furthermore, the radicals $R_{17}$ and $R_{18}$ together with the carbon atoms to which they are attached form a $C_5$–$C_{12}$cycloalkylene ring which is unsubstituted or substituted by 1 to 3 $C_1$–$C_4$alkyl groups; or, if $R_6$, $R_{17}$ and $R_{19}$ are hydrogen, $R_4$ is not a radical of the formula (2), m is 1 and $R_1$ is as defined above for m=1, $R_{18}$ is additionally a radical of the formula (4)

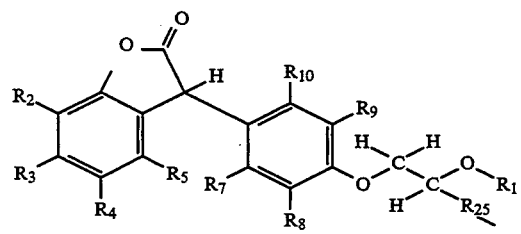

(4)

$R_{19}$ is hydrogen or $C_1$–$C_4$alkyl,
$R_{20}$ is hydrogen or $C_1$–$C_4$alkyl,
$R_{21}$ is a direct bond, $C_1$–$C_{18}$alkylene, $C_2$–$C_{18}$alkylene which is interrupted by oxygen, sulfur or

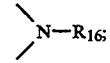

$C_2$–$C_{18}$alkenylene, $C_2$–$C_{20}$alkylidene, $C_7$–$C_{20}$phenylalkylidene, $C_5$–$C_8$-cycloalkylene, $C_7$–$C_8$-bicycloalkylene, unsubstituted or $C_1$–$C_4$alkyl-substituted phenylene,

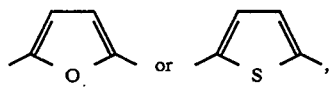

$R_{22}$ is oxygen,

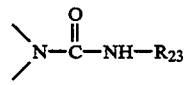

$R_{23}$ is $C_1$–$C_{18}$alkylene or phenyl,
$R_{24}$ is $C_2$–$C_{18}$alkylene, $C_5$–$C_{18}$cycloalkylene or phenylene, $R_{25}$ is a direct bond, $C_1$–$C_{18}$alkylene or $C_2$–$C_{18}$alkylene which is interrupted by oxygen, sulfur or

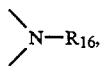

M is an r-valent metal cation, m is 1, 2, 3 or 4, $R_6$ being hydrogen if m is 2, 3 or 4;

n is 0, 1 or 2 and r is 1, 2 or 3.

Alkanoyl of up to 25 carbon atoms is a branched or unbranched radical, for example formyl, acetyl, propionyl, butanoyl, pentanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, eicosanoyl or docosanoyl. A preferred meaning of $R_1$ is $C_1$–$C_{18}$alkanoyl. An especially preferred meaning of $R_1$ is $C_2$–$C_4$alkanoyl.

Alkenoyl of 3 to 25 carbon atoms is a branched or unbranched radical, for example propenoyl, 2-butenoyl, 3-butenoyl, isobutenoyl, n-2,4-pentadienoyl, 3-methyl-2-butenoyl, n-2-octenoyl, n-2-dodecenoyl, iso-dodecenoyl, oleoyl, n-2-octadecenoyl or n-4-octadecenoyl.

Examples of $C_3$–$C_{25}$alkanoyl which is interrupted by oxygen, sulfur or

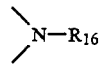

are $CH_3$—O—$CH_2CO$—, $CH_3$—S—$CH_2CO$—, $CH_3$—NH—$CH_2CO$—, $CH_3$—N($CH_3$)—$CH_2CO$—, $CH_3$—O—$CH_2CH_2$—O—$CH_2CO$—, $CH_3$—(O—$CH_2CH_2$—)$_2$O—$CH_2CO$—, $CH_3$—(O—$CH_2CH_2$—)$_3$O—$CH_2CO$— or $CH_3$—(O—$CH_2CH_2$—)$_4$O—$CH_2CO$—. Methoxyacetyl is preferred.

Examples of $C_2$–$C_{25}$alkanoyl which is substituted by a di($C_1$–$C_6$alkyl)phosphonate group are ($CH_3CH_2O$)$_2$POCH$_2$CO—, ($CH_3O$)$_2$POCH$_2$CO—, ($CH_3CH_2CH_2CH_2O$)$_2$POCH$_2$CO—, ($CH_3CH_2O$)$_2$POCH$_2$CH$_2$CO—, ($CH_3O$)$_2$POCH$_2$CH$_2$CO—, ($CH_3CH_2CH_2CH_2O$)$_2$POCH$_2$CH$_2$CO—, ($CH_3CH_2O$)$_2$PO(CH$_2$)$_4$CO—, ($CH_3CH_2O$)$_2$PO(CH$_2$)$_8$CO— or ($CH_3CH_2O$)$_2$PO(CH$_2$)$_{17}$CO—.

Examples of $C_6$–$C_9$cycloalkylcarbonyl are cyclopentylcarbonyl, cyclohexylcarbonyl, cycloheptylcarbonyl or cyclooctylcarbonyl. Cyclohexylcarbonyl is preferred.

Examples of $C_1$–$C_{12}$alkyl-substituted benzoyl are o-, m- or p-methylbenzoyl, 2,3-dimethylbenzoyl, 2,4-dimethylbenzoyl, 2,5-dimethylbenzoyl, 2,6-dimethylbenzoyl, 3,4-dimethylbenzoyl, 3,5-dimethylbenzoyl, 2-methyl-6-ethylbenzoyl, 4-ten-butylbenzoyl, 2-ethylbenzoyl, 2,4,6-trimethylbenzoyl, 2,6-dimethyl-4-tert-butylbenzoyl or 3,5-ditert-butylbenzoyl.

$C_4$–$C_{18}$Alkanetricarbonyl is a branched or unbranched radical, for example methanetricarbonyl, 1,1,2-ethanetricarbonyl, 1,2,3-propanetricarbonyl or 1,2,3-butanetricarbonyl.

Examples of $C_9$–$C_{18}$aryltricarbonyl am 1,2,4-benzenetricarbonyl (derived from trimellitic acid) or 1,3,5-benzenetricarbonyl (derived from trimesic acid).

$C_6$–$C_{18}$Alkanetetracarbonyl is a branched or unbranched radical, for example 1,1,3,3-propanetetracarbonyl or 1,2,3,4-butanetetracarbonyl.

An example of $C_{10}$–$C_{18}$aryltetracarbonyl is 1,2,4,5-benzenetetracarbonyl (derived from pyromellitic acid).

Alkyl of up to 25 carbon atoms is a branched or unbranched radical, for example methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl, octadecyl, eicosyl or docosyl. An example of one of the preferred meanings of $R_2$ and $R_4$ is $C_1$–$C_{18}$alkyl. A particularly preferred meaning of $R_4$ is $C_1$–$C_4$alkyl.

Examples of $C_7$–$C_9$phenylalkyl are benzyl, α-methylbenzyl, α,α-dimethylbenzyl or 2-phenylethyl. Benzyl is preferred.

Examples of $C_1$–$C_4$alkyl-substituted phenyl which preferably contains 1 to 3, in particular 1 or 2, alkyl groups are o-, m- or p-methylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2-methyl-6-ethylphenyl, 4-tert-butylphenyl, 2-ethylphenyl or 2,6-diethylphenyl.

Examples of unsubstituted or $C_1$–$C_4$alkyl-substituted $C_5$–$C_8$cycloalkyl are cyclopentyl, methylcyclopentyl, dimethylcyclopentyl, cyclohexyl, methylcyclohexyl, dimethylcyclohexyl, trimethylcyclohexyl, tert-butylcyclohexyl, cycloheptyl or cyclooctyl. Cyclohexyl and tert-butylcyclohexyl are preferred.

Alkoxy of up to 18 carbon atoms is a branched or unbranched radical, for example methoxy, ethoxy, propoxy, isopropoxy, n-butoxy, isobutoxy, pentoxy, isopentoxy, hexoxy, heptoxy, octoxy, decyloxy, tetradecyloxy, hexadecyloxy or octadecyloxy.

Alkylthio of up to 18 carbon atoms is a branched or unbranched radical, for example methylthio, ethylthio, propylthio, isopropylthio, n-butylthio, isobutylthio, pentylthio, isopentylthio, hexylthio, heptylthio, octylthio, decylthio, tetradecylthio, hexadecylthio or octadecylthio.

Alkylamino of up to 4 carbon atoms is a branched or unbranched radical, for example methylamino, ethylamino, propylamino, isopropylamino, n-butylamino, isobutylamino or tert-butylamino.

Di-($C_1$–$C_4$alkyl)amino also means that the two radicals are branched or unbranched independently of one another, for example dimethylamino, methylethylamino, diethylamino, methyl-n-propylamino, methylisopropylamino, methyl-n-butylamino, methylisobutylamino, ethylisopropylamino, ethyl-n-butylamino, ethylisobutylamino, ethyl-tert-butylamino, diethylamino, diisopropylamino, isopropyl-n-butylamino, isopropylisobutylamino, di-n-butylamino or diisobutylamino.

Alkanoyloxy of up to 25 carbon atoms is a branched or unbranched radical, for example formyloxy, acetyloxy, propionyloxy, butanoyloxy, pentanoyloxy, hexanoyloxy, heptanoyloxy, octanoyloxy, nonanoyloxy, decanoyloxy, undecanoyloxy, dodecanoyloxy, tridecanoyloxy, tetradecanoyloxy, pentadecanoyloxy, hexadecanoyloxy, heptadecanoyloxy, octadecanoyloxy, eicosanoyloxy or docosanoyloxy.

Alkanoylamino of up to 25 carbon atoms is a branched or unbranched radical, for example formylamino, acetylamino, propionylamino, butanoylamino, pentanoylamino, hexanoylamino, heptanoylamino, octanoylamino, nonanoylamino, decanoylamino, undecanoylamino, dodecanoylamino, tridecanoylamino, tetradecanoylamino, pentadecanoylamino, hexadecanoylamino, heptadecanoylamino, octadecanoylamino, eicosanoylamino or docosanoylamino.

Alkenoyloxy of 3 to 25 carbon atoms is a branched or unbranched radical, for example propenoyloxy, 2-butenoyloxy, 3-butenoyloxy, isobutenoyloxy, n-2,4-pentadienoyloxy, 3-methyl-2-butenoyloxy, n-2-octenoyloxy, n-2-dodecenoyloxy, iso-dodecenoyloxy, oleoyloxy, n-2-octadecenoyloxy or n-4-octadecenoyloxy.

Examples of $C_3$-$C_{25}$alkanoyloxy which is interrupted by oxygen, sulfur or

are $CH_3$—O—$CH_2$COO—, $CH_3$—S—$CH_2$COO—, $CH_3$—NH—$CH_2$COO—, $CH_3$—N($CH_3$)—$CH_2$COO—, $CH_3$—O—$CH_2CH_2$—O—$CH_2$COO—, $CH_3$—(O—$CH_2CH_2$—)$_2$O—$CH_2$COO—, $CH_3$—(O—$CH_2CH_2$—)$_3$O—$CH_2$COO—oder $CH_3$—(O—$CH_2CH_2$—)$_4$O—$CH_2$COO—.

Examples of $C_6$-$C_9$cycloalkylcarbonyloxy are cyclopentylcarbonyloxy, cyclohexylcarbonyloxy, cycloheptylcarbonyloxy or cyclooctylcarbonyloxy. Cyclohexylcarbonyloxy is preferred.

Examples of $C_1$-$C_{12}$alkyl-substituted benzoyloxy are o-, m- or p-methylbenzoyloxy, 2,3-dimethylbenzoyloxy, 2,4-dimethylbenzoyloxy, 2,5-dimethylbenzoyloxy, 2,6-dimethylbenzoyloxy, 3,4-dimethylbenzoyloxy, 3,5-dimethylbenzoyloxy, 2-methyl-6-ethylbenzoyloxy, 4-tert-butylbenzoyloxy, 2-ethylbenzoyloxy, 2,4,6-trimethylbenzoyloxy, 2,6-dimethyl4-tert-butylbenzoyloxy or 3,5-di-tert-butylbenzoyloxy.

A $C_1$-$C_4$alkyl-substituted $C_5$-$C_8$cycloalkylidene ring that preferably contains 1 to 3, most preferably 1 or 2, branched or unbranched alkyl groups, is typically cyclopentylidene, methylcyclopentylidene, dimethylcyclopentylidene, cyclohexylidene, methylcyclohexylidene, dimethylcyclohexylidene, trimethylcyclohexylidene, tert-butylcyclohexylidene, cycloheptylidene or cyclooctylidene. Cyclohexylidene and tert-butylcyclohexylidene are preferred.

Examples of $C_1$-$C_4$alkyl-substituted $C_5$-$C_{12}$cycloalkylene rings which preferably contain 1 to 3, in particular 1 or 2, branched or unbranched alkyl group radicals are cyclopentylene, methylcyclopentylene, dimethylcyclopentylene, cyclohexylene, methylcyclohexylene, dimethylcyclohexylene, trimethylcyclohexylene, tert-butylcyclohexylene, cycloheptylene, cyclooctylene or cyclodecylene. Cyclohexylene and tert-butylcyclohexylene are preferred.

Examples of $C_2$-$C_{25}$alkyl which is interrupted by oxygen, sulfur or

are $CH_3$—O—$CH_2$—, $CH_3$—S—$CH_2$—, $CH_3$—NH—$CH_2$—, $CH_3$—N($CH_3$)—$CH_2$—, $CH_3$—O—$CH_2$—, $CH_3$—(O—$CH_2CH_2$—)$_2$O—$CH_2$—, $CH_3$—(O—$CH_2CH_2$—)$_3$O—$CH_2$—oder $CH_3$—(O—$CH_2CH_2$—)$_4$O—$CH_2$—.

Examples of $C_7$-$C_9$phenylalkyl which is unsubstituted or substituted on the phenyl radical by 1 to 3 $C_1$-$C_4$alkyl groups are benzyl, αmethylbenzyl, α,α-dimethylbenzyl, 2-phenylethyl, 2-methylbenzyl, 3-methylbenzyl, 4-methylbenzyl, 2,4-dimethylbenzyl, 2,6-dimethylbenzyl or 4-tert-butylbenzyl. Benzyl is preferred.

$C_7$-$C_{25}$Phenylalkyl which is interrupted by oxygen, sulfur or

and unsubstituted or substituted on the phenyl radical by 1 to 3 $C_1$-$C_4$alkyl groups is a branched or unbranched radical, for example phenoxymethyl, 2-methylphenoxymethyl, 3-methyl-phenoxymethyl, 4-methylphenoxymethyl, 2,4-dimethylphenoxymethyl, 2,3-dimethylphenoxymethyl, phenylthiomethyl, N-methyl-N-phenylmethyl, N-ethyl-N-phenylmethyl, 4-tert-butylphenoxymethyl, 4-tert-butylphenoxyethoxymethyl, 2,4-di-tertbutylphenoxymethyl, 2,4-di-tert-butylphenoxyethoxymethyl, phenoxyethoxyethoxymethyl, benzyloxymethyl, benzyloxyethoxymethyl, N-benzyl-N-ethylmethyl or N-benzyl-N-isopropylmethyl.

$C_1$-$C_{18}$Alkylene is a branched or unbranched radical, for example methylene, ethylene, propylene, butylene, pentamethylene, hexamethylene, heptamethylene, octamethylene, decamethylene, dodecamethylene or octadecamethylene. $C_1$-$C_8$Alkylene is preferred.

Examples of $C_2$-$C_{18}$alkylene which is interrupted by oxygen, sulfur or

are —$CH_2$—O—$CH_2$—, —$CH_2$—S—$CH_2$—, —$CH_2$—NH—$CH_2$—, —$CH_2$—N($CH_3$)—$CH_2$—, —$CH_2$—O—$CH_2CH_2$—O—$CH_2$—, —$CH_2$—(O—$CH_2CH_2$—)$_2$O—$CH_2$—, —$CH_2$—(O—$CH_2CH_2$—)—$CH_2$—(O—$CH_2CH_2$—)$_4$O—$CH_2$— or —$CH_2CH_2$—S—$CH_2CH_2$—.

Examples of $C_2$-$C_{18}$alkenylene are vinylene, methylvinylene, octenylethylene or dodecenylethylene. $C_2$-$C_8$Alkenylene is preferred.

Examples of alkylidene having 2 to 20 carbon atoms are ethylidene, propylidene, butylidene, pentylidene, 4-methylpentylidene, heptylidene, nonylidene, tridecylidene, nonadecylidene, 1-methylethylidene, 1-ethylpropylidene or 1-ethylpentylidene. $C_2$-$C_8$Alkylidene is preferred.

Examples of phenylalkylidene having 7 to 20 carbon atoms are benzylidene, 2-phenyl-ethylidene or 1-phenyl-2-hexylidene. $C_7$-$C_9$Phenylalkylidene is preferred.

$C_5$-$C_8$Cycloalkylene is a saturated hydrocarbon group having two free valencies and at least one ring unit and is, for example, cyclopentylene, cyclohexylene, cycloheptylene or cyclooctylene. Cyclohexylene is preferred.

Examples of $C_7$-$C_8$bicycloalkylene are bicycloheptylene or bicyclooctylene. Examples of unsubstituted or $C_1$-$C_4$alkyl-substituted phenylene are 1,2-, 1,3- or 1,4-phenylene.

$C_2$-$C_{18}$Alkylene is a branched or unbranched radical for example ethylene, propylene, butylene, pentamethylene, hexamethylene, heptamethylene, octamethylene, decamethylene, dodecamethylene or octadecamethylene. $C_2$-$C_8$Alkylene is preferred.

A mono-, di- or trivalent metal cation is preferably an alkali metal cation, alkaline earth metal cation or aluminium cation, for example $Na^+$, $K^+$, $Mg^{++}$, $Ca^{++}$ or $Al^{+++}$.

Preference is given to compounds of the formula (1) in which,
if m is 1,
$R_1$ is hydrogen, $C_1$-$C_{18}$alkanoyl, $C_3$-$C_{18}$alkenoyl, $C_3$-$C_{18}$alkanoyl which is interrupted by oxygen, sulfur or

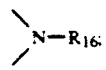

$C_2$-$C_{18}$alkanoyl which is substituted by a di($C_1$-$C_6$alkyl)-phosphonate group; $C_6$-$C_9$cycloalkylcarbonyl, thenoyl, furoyl, benzoyl or $C_1$-$C_8$alkyl-substituted benzoyl;

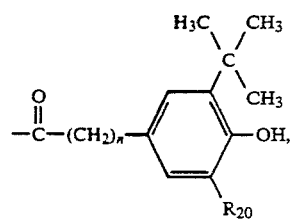

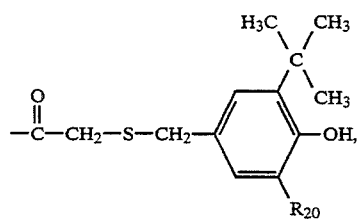

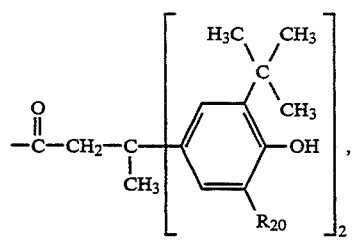

-continued

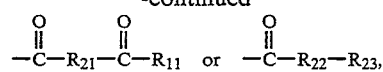

$R_2$, $R_3$, $R_4$ and $R_5$, independently of one another, are hydrogen, chlorine, $C_1$-$C_{18}$alkyl, benzyl, phenyl, $C_5$-$C_8$cycloalkyl, $C_1$-$C_{18}$alkoxy, $C_1$-$C_{18}$alkylthio, $C_1$-$C_{18}$alkanoyloxy, $C_1$-$C_{18}$alkanoylamino, $C_3$-$C_{18}$alkenoyloxy or benzoyloxy, or, furthermore, the radicals $R_2$ and $R_3$ or the radicals $R_4$ and $R_5$ together with the carbon atoms to which they are attached form a phenyl ring, or, if $R_3$, $R_5$, $R_6$, $R_7$ and $R_{10}$ are hydrogen, $R_4$ is additionally a radical of the formula (2), $R_7$, $R_8$, $R_9$ and $R_{10}$, independently of one another, are hydrogen or $C_1$-$C_4$alkyl, on the condition that at least one of the radicals $R_7$, $R_8$, $R_9$ and $R_{10}$ is hydrogen, $R_{12}$ and $R_{13}$ are methyl groups or together with the C atom to which they are attached form a $C_5$-$C_8$cycloalkylidene ring which is unsubstituted or substituted by 1 to 3 $C_1$-$C_4$alkyl groups, $R_{18}$ is hydrogen, phenyl, $C_2$-$C_{18}$alkyl, $C_2$-$C_{18}$alkyl which is interrupted by oxygen, sulfur or

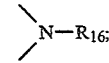

benzyl, $C_7$-$C_{18}$phenylalkyl which is interrupted by oxygen, sulfur or

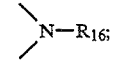

or, furthermore, the radicals $R_{17}$ and $R_{18}$ together with the carbon atoms to which they are attached form a $C_5$-$C_8$cycloalkylene ring which is unsubstituted or substituted by 1 to 3 $C_1$-$C_4$alkyl groups, $R_{21}$ is a direct bond, $C_1$-$C_{12}$alkylene, $C_2$-$C_{12}$alkylene which is interrupted by oxygen, sulfur or

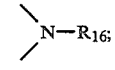

$C_2$-$C_{12}$alkenylene, $C_2$-$C_{12}$alkylidene, $C_7$-$C_{12}$phenylalkylidene, $C_5$-$C_8$-cycloalkylene, $C_7$-$C_8$-bicycloalkylene or phenylene, $R_{24}$ is $C_2$-$C_{12}$alkylene, $C_5C_8$acycloalkylene or phenylene, and $R_{25}$ is a direct bond, $C_1$-$C_{12}$alkylene or $C_2$-$C_{12}$alkylene which is interrupted by oxygen, sulfur or

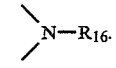

Preference is also given to compounds of the formula (1) in which at least two of the radicals $R_2$, $R_3$, $R_4$ and $R_5$ are hydrogen.

Likewise, preference is given to compounds of the formula (1) in which $R_3$ and $R_5$ are hydrogen.

Particular preference is given to compounds of the formula (1) in which $R_2$, $R_3$, $R_4$ and $R_5$, independently of one another, are hydrogen, chlorine, $C_1$–$C_{18}$alkyl, $C_5$–$C_6$cycloalkyl or $C_1$–$C_4$alkoxy or, furthermore, the radicals $R_2$ and $R_3$ together with the carbon atoms to which they are attached form a phenyl ring.

Likewise, particular preference is given to compounds of the formula (1) in which m is 1 or 2.

Of particular interest are compounds of the formula (1) in which $R_{18}$ is hydrogen, $C_1$–$C_{12}$-alkyl, $C_2$–$C_{12}$alkyl which is interrupted by oxygen or sulfur; $C_7$–$C_{12}$phenylalkyl which is interrupted by oxygen or sulfur, or, furthermore, the radicals $R_{17}$ and $R_{18}$ together with the carbon atoms to which they are attached form a $C_5$–$C_8$-cycloalkylene ring.

Of particular interest are also compounds of the formula (1) in which,
if m is 1,
$R_1$ is hydrogen, $C_1$–$C_{18}$alkanoyl, $C_3$–$C_{12}$alkenoyl, $C_3$–$C_{12}$alkanoyl which is interrupted by oxygen; $C_2$–$C_{12}$alkanoyl which is substituted by a di($C_1$–$C_6$-alkyl)phosphonate group; $C_6$–$C_9$cycloalkylcarbonyl, benzoyl,

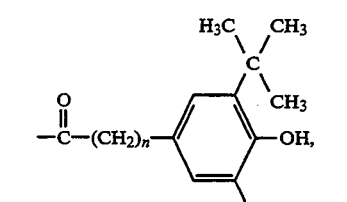

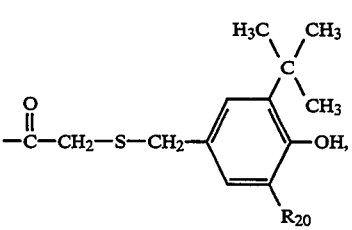

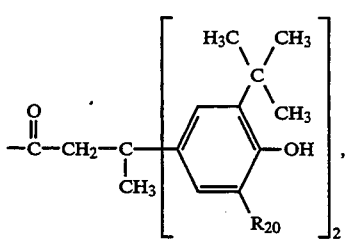

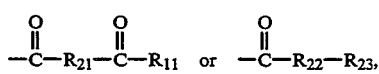

$R_2$, $R_3$, $R_4$ and $R_5$ independently of one another, are hydrogen, $C_1$–$C_{18}$alkyl, $C_5$–$C_7$cycloalkyl, $C_1$–$C_{12}$alkoxy, $C_1$–$C_{12}$alkanoyloxy or benzoyloxy, or, furthermore, the radicals $R_2$ and $R_3$ together with the carbon atoms to which they are attached form a phenyl ring, or, if $R_3$, $R_5$, $R_6$, $R_7$ and $R_{10}$ are hydrogen, $R_4$ is additionally a radical of the formula (2), $R_{12}$ and $R_{13}$ are methyl groups or together with the C atom to which they are attached form a $C_5$–$C_8$cycloalkylidene ring, $R_{18}$ is hydrogen, $C_2$–$C_{12}$alkyl, $C_2$–$C_{12}$alkyl which is interrupted by oxygen or sulfur;
$C_7$–$C_{12}$phenylalkyl which is interrupted by oxygen or sulfur, or, furthermore, the radicals
$R_{17}$ and $R_{18}$ together with the carbon atoms to which they are attached form a $C_5$–$C_8$cycloalkylene ring,
$R_{21}$ is $C_1$–$C_{12}$alkylene, phenylene or $C_2$–$C_{12}$alkylene which is interrupted by oxygen or sulfur,
$R_{23}$ is $C_1$–$C_{12}$alkyl,
$R_{24}$ is $C_2$–$C_{12}$alkylene, or phenylene,
$R_{25}$ is $C_1$–$C_8$alkylene or $C_2$–$C_8$alkylene which is interrupted by oxygen, and
m is 1, 2 or 3.

Of particular interest are specifically compounds of the formula (1) in which,
if m is 1,
$R_1$ is hydrogen, $C_1$–$C_{18}$alkanoyl, $C_3$–$C_4$alkenoyl, $C_2$–$C_4$alkanoyl which is substituted by a di($C_1$–$C_4$alkyl)phosphonate group; cyclohexylcarbonyl, benzoyl,

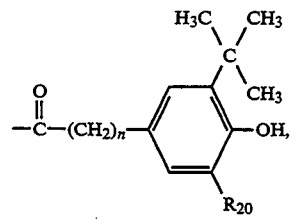

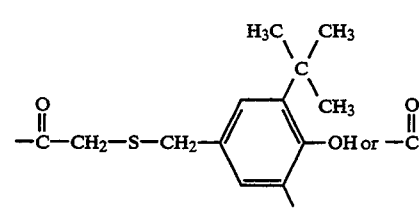

if m is 2,
$R_1$ is

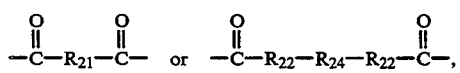

$R_2$ is hydrogen, $C_1$–$C_{18}$alkyl or cyclohexyl,
$R_3$ is hydrogen, or, furthermore, the radicals $R_2$ and $R_3$ together with the carbon atoms to which they are attached form a phenyl ring,
$R_4$ is $C_1$–$C_4$alkyl or cyclohexyl, or, if $R_3$, $R_5$, $R_6$, $R_7$ and $R_{10}$ are hydrogen, $R_4$ is additionally a radical of the formula (2), in which $R_1$ is as defined above for m=1,
$R_5$ is hydrogen,
$R_6$ is hydrogen or a radical of the formula (3), in which $R_4$ is not a radical of the formula (2) and $R_1$ being as defined above for m=1,
$R_7$ is hydrogen,
$R_8$ and $R_9$, independently of one another, are hydrogen, $C_1$–$C_4$alkyl or $C_1$–$C_4$alkoxy,
$R_{10}$ is hydrogen,
$R_{12}$ and $R_{13}$ are methyl groups or, together with the C atom to which they are attached, form a cyclohexylidene ring, $R_{17}$ is hydrogen, $R_{18}$ is hydrogen, $C_1$–$C_4$alkyl, $C_2$–$C_8$alkyl which is interrupted by oxygen; or $C_7$–$C_9$phenylalkyl which is interrupted by oxygen, or, furthermore, the radicals $R_{17}$ and $R_{18}$ together with the carbon atoms to which they are attached form a cyclohexylene ring, $R_{19}$ is hydrogen, $R_{20}$ is hydrogen or $C_1$–$C_4$alkyl, $R_{21}$ is $C_1$–$C_3$alkylene, $C_2$–$C_6$alkylene which is interrupted by sulfur; or phenylene, $R_{22}$ is —NH— or

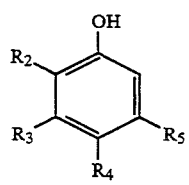

$R_{23}$ is $C_1$–$C_4$alkyl, $R_{24}$ is $C_4$–$C_8$alkylene, m is 1 or 2, and n is 0 or 2.

The compounds according to the invention of the formula (1) can be prepared in a manner known per se.

For example, this being the preferred method, a phenol of the formula (5)

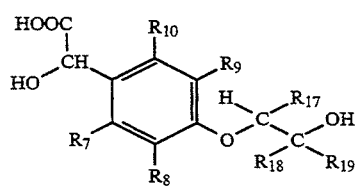

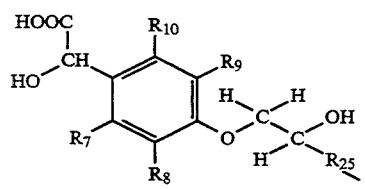

in which $R_2$, $R_3$, $R_4$ and $R_5$ are as defined, is reacted with a mandelic acid derivative of the formula (6) which is substituted on the phenyl ring and in which $R_7$, $R_8$, $R_9$, $R_{10}$, $R_{17}$, $R_{18}$ and $R_{19}$ are as defined above and, $R_{17}$ and $R_{19}$ are hydrogen, $R_{18}$ is additionally a radical of the formula (10)

in which $R_7$, $R_8$, $R_9$, $R_{10}$ and $R_{25}$ are as defined above, at elevated temperature, in particular at temperatures from 130° to 200° C., in melted form or in a solvent, if desired under a slight vacuum, to give compounds of the formula (7)

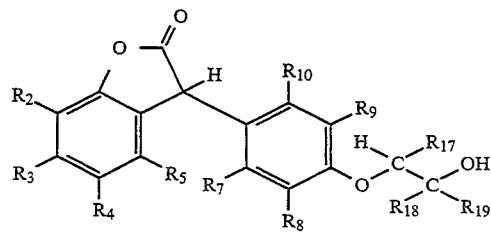

The reaction is preferably carried out in a solvent, for example acetic acid, propionic acid or formic acid, in a temperature range from 50° to 130° C. The reaction can be catalyzed by addition of an acid, such as hydrochloric acid, sulfuric acid or methanesulfonic acid. The reaction can be carried out, for example, in the manner described in the references given in the introduction to the description.

The alcohols of the formula (7) obtained by this reaction can be esterified by generally known esterification methods, for example according to Organikum 1986, page 402–408, for example by acylation with an acid chloride or acid anhydride of the formula $R_1{}^1Cl$ or $R_1{}^1$—O—$R_1{}^1$, in which $R_1{}^1$ is $R_1$ with the exception of hydrogen, to give the compounds of the formula (1). If, instead of an acid chloride, an isocyanate of the formula $R_{23}$—N=C=O is used as the reagent, the corresponding carbamates of the formula (1) are obtained, in which $R_1$ is a radical

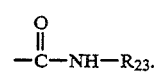

The compounds according to the invention of the formula (1) can be present in different crystal modifications.

The alcohols of the formula (7) can likewise be reacted by generally known transesterification methods, for example according to Organikum 1986, page 388, for example by transesterification with ,

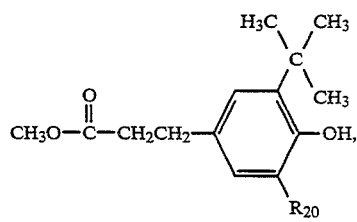

to give the compounds of the formula (1). The methanol formed in the reaction is continuously distilled off.

The 3-(2-hydroxyethoxyphenyl)benzofuran-2-ones of the formula (7) can also be reacted directly, without being isolated or purified, with acid chlorides or acid anhydrides to give the 3-(2-acyloxyethoxyphenyl)benzofuran-2-ones of the formula (1).

The reaction of the compounds of the formula (5) and (6) is preferably carried out by boiling the two components in a carboxylic acid solvent, for example acetic acid or propionic acid. The water of reaction is removed by distillation, advantageously by azeotropic distillation or by addition of the acid chloride which corresponds to the solvent, for example acetyl chloride or propionyl chloride, or of the acid anhydride, for example acetic anhydride or propionic anhydride. In that case, the products obtained are the corresponding 3-(2-acyloxyethoxyphenyl)benzofuran-2-ones of the formula (1).

The 3-(2-hydroxyethoxyphenyl)benzofuran-2-ones of the formula (7) are also obtainable by hydrolysis or alcoholysis of the 3-(2-acyloxyethoxyphenyl)benzofuran-2-ones of the formula (1). The reaction is preferably carried out in refluxing methanol to which concentrated hydrochloric acid is added.

The phenols of the formula (5) are known or can be obtained by methods known per se.

Bisphenol compounds of the formula (8)

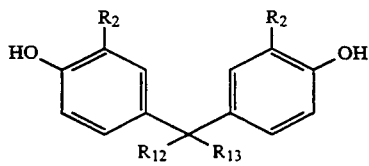

can be prepared according to Houben-Weyl, Methoden der organischen Chemie, Volume 6/1c, 1030.

4-(2-Hydroxyethoxy)mandelic acids are largely unknown in the literature. Only the unsubstituted 4-(2-hydroxyethoxy)mandelic acid has been described in EP-A-146 269 and EP-A-397 170.

Accordingly, the present invention also provides compounds of the formula (9)

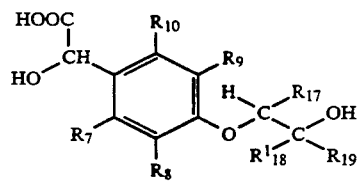

in which $R_7$, $R_8$, $R_9$ and $R_{10}$, independently of one another, are hydrogen, $C_1$-$C_4$alkyl or $C_1$-$C_4$alkoxy, on the condition that at least one of the radicals $R_7$, $R_8$, $R_9$ and $R_{10}$ is hydrogen and, if $R_7$, $R_8$, $R_9$ and $R_{10}$ are simultaneously hydrogen, either $R_{17}$, $R_{18}^1$ or $R_{19}$ is different from hydrogen, $R_{16}$ is hydrogen or $C_1$-$C_8$alkyl, $R_{17}$ is hydrogen or $C_1$-$C_4$alkyl, $R_{18}$ is hydrogen, unsubstituted or $C_1$-$C_4$alkyl-substituted phenyl; $C_1$-$C_{25}$alkyl, $C_2$-$C_{25}$alkyl which is interrupted by oxygen or sulfur; $C_7$—$C_9$phenylalkyl which is unsubstituted or substituted on the phenyl ring by 1 to 3 $C_1$-$C_4$alkyl groups; $C_7$-$C_{25}$-phenylalkyl which is interrupted by oxygen, sulfur or

and unsubstituted or substituted on the phenyl ring by 1 to 3 $C_1$-$C_4$alkyl groups, or, furthermore, the radicals $R_{17}$ and $R_{18}^1$ together with the carbon atoms to which they are attached form a $C_5$-$C_{12}$cycloalkylene ring which is unsubstituted or substituted by 1 to 3 $C_1$-$C_4$alkyl groups; or, if $R_{17}$ and $R_{19}$ are hydrogen, $R_{18}^1$ is additionally a radical of the formula (10)

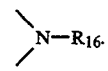

$R_{19}$ is hydrogen or $C_1$-$C_4$alkyl, and $R_{25}$ is a direct bond, $C_1$-$C_{18}$alkylene or $C_2$-$C_{18}$alkylene which is interrupted by oxygen, sulfur or

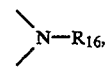

Preference is given to compounds of the formula (9) in which $R_{18}^1$ is hydrogen, phenyl, $C_1$-$C_{18}$alkyl, $C_2$-$C_{18}$alkyl which is interrupted by oxygen or sulfur; benzyl, $C_7$-$C_{18}$phenylalkyl which is interrupted by oxygen, sulfur or

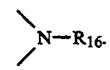

or, furthermore, the radicals $R_{17}$ and $R_{18}^1$ together with the carbon atoms to which they are attached form a $C_5$-$C_8$cycloalkylene ring which is unsubstituted or substituted by 1 to 3 $C_1$-$C_4$alkyl groups, and $R_{25}$ is a direct bond, $C_1$-$C_{12}$alkylene or $C_2$-$C_{12}$alkylene which is interrupted by oxygen, sulfur or

>N—R_{16}.

Likewise, preference is given to compounds of the formula (9) in which $R_7$ and $R_{10}$ are hydrogen.

Particular preference is given to compounds of the formula (9) in which $R_{17}$ is hydrogen, $R_{18}^1$ is hydrogen, $C_1$-$C_{12}$alkyl, $C_2$-$C_{12}$alkyl which is interrupted by oxygen or sulfur;

$C_7$-$C_{12}$phenylalkyl which is interrupted by oxygen or sulfur, or, furthermore, the radicals $R_{17}$ and $R_{18}^1$ together with the carbon atoms to which they are attached form a $C_5$-$C_8$-cycloalkylene ring, and $R_{25}$ is $C_1$-$C_8$alkylene or $C_2$-$C_8$alkylene which is interrupted by oxygen.

Of particular interest are specifically compounds of the formula (9) in which $R_7$, $R_{10}$, $R_{17}$ and $R_{19}$ are hydrogen, and $R_{18}^1$ is hydrogen, $C_1$-$C_4$alkyl, $C_2$-$C_8$alkyl which is interrupted by oxygen; $C_7$-$C_9$phenylalkyl which is interrupted by oxygen, or, furthermore, the radicals $R_{17}$ and $R_{18}^1$ together with the carbon atoms to which they are attached form a cyclohexylene ring.

The compounds of the formulae (6) and (9) can be prepared in a manner known per se. Both EP-A-146 269 and EP-A-397 170 describe alkylation of 4-hydroxymandelic acid of the formula (11), in which $R_7$, $R_8$, $R_9$ and $R_{10}$ are hydrogen, with bromoethanol under basic conditions to give 4-(2-hydroxyethoxy)mandelic acid.

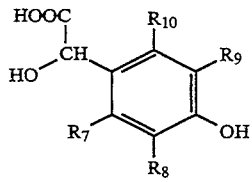

(11)

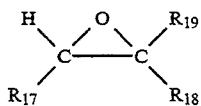

(12)

Furthermore, it has now been found that the reaction of 4-hydroxymandelic acids of the formula (11) with epoxides of the formula (12) proceeds very easily and in good yield to give the 4-(2-hydroxyethoxyphenyl)mandelic acids of the formulae (6) and (9).

Accordingly, the invention also provides a novel process for preparing compounds of the formula (6),

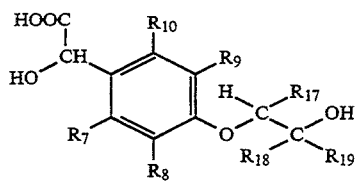

(6)

in which the general symbols are as defined in formula (1) and, if $R_{17}$ and $R_{19}$ are hydrogen, $R_{18}$ is additionally a radical of the formula (10)

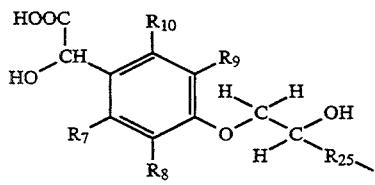

(10)

which comprises reacting a 4-hydroxymandelic acid of the formula (11) with an epoxide of the formula (12),

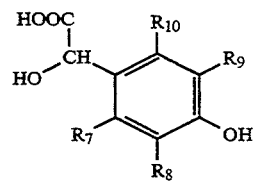

(11)

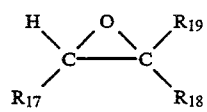

(12)

in which the radicals $R_7$, $R_8$, $R_9$, $R_{10}$, $R_{17}$, $R_{18}$ and $R_{19}$ have the same meaning as described for formula (1) and, if $R_{17}$ and $R_{19}$ are hydrogen, $R_{18}$ in formula (12) is additionally a radical of the formula (10) or a radical of the formula (16)

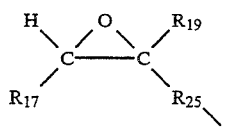

(16)

to give compounds of the formula (6).

Of particular interest is a process for preparing compounds of the formula (6) in which $R_{18}$ has the same meaning as described for formula (1).

The preferred radicals $R_7$, $R_8$, $R_9$, $R_{10}$, $R_{17}$, $R_{18}$ and $R_{19}$ in the process for preparing the compounds of the formula (6) are identical to those described for the compound of the formula (1).

The reaction is preferably carried out in the presence of a base in a temperature range from 20° to 200° C., in particular 50° to 150° C., and under slight pressure.

The base used, for example sodium hydroxide, is used in equimolar amounts or a slight excess, in particular an excess of 1 to 30%, relative to the 4-hydroxymandelic acid used. In the case where the 4-hydroxymandelic acid is used in the form of its salts, in particular sodium salts, a correspondingly small amount of base is used.

The reaction can be carried out in the presence or absence of solvent. However, it is preferred to use a solvent, in particular water.

A particularly preferred epoxide of the formula (12) is ethylene oxide. In a particularly preferred process, the epoxide is used in a molar excess of 1 to 80%, in particular 10 to 60%, relative to the 4-hydroxymandelic acid of the formula (10) used.

The mandelic acids of the formula (11) which are substituted on the phenyl ring are known in the literature or can be prepared analogously for example according to W. Bradley et al., J. Chem. Soc. 1956, 1622; EP-A-146 269, EP-B-182 507 (Example 1, page 4) or DE-A-2 944 295.

Epoxides of the formula (12) are known in the literature or can be easily obtained by oxidation of the corresponding olefins with peracids. The particularly preferred ethylene oxide is prepared on a large industrial scale. Preference is also given to alkylation of an alcohol or phenol $R_{18}{}^2OH$ with epichlorohydrin (1-chloro-2,3-epoxy-propane) to give epoxides of the formula

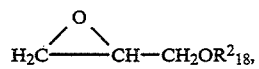

in which the radical $-CH_2OR_{18}{}^2$ is included in the range of definitions for $R_{18}$.

It is of course also possible first to react the 4-hydroxymandelic acids of the formula (11) which are substituted on the phenyl ring at elevated temperature, in particular temperatures of 130° to 200° C., in melted form or in a solvent, if desired under slight vacuum, to give compounds of the formula (13)

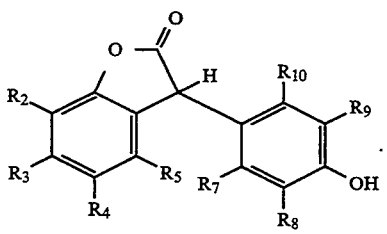

Preferably, the reaction is carried out in a solvent, for example acetic acid, propionic acid or formic acid, in a temperature range from 50° to 130° C. The reaction can be catalyzed by addition of an acid, such as hydrochloric acid, sulfuric acid or methanesulfonic acid. The reaction can be carried out, for example, in the manner described in the references given in the introduction to the description.

The reaction of the compounds of the formula (13) with either the epoxides of the formula (12) or haloethanol (bromoethanol or chloroethanol) give the 3-(2-hydroxyethoxyphenyl)benzofuran-2-ones of the formula (7) in a manner analogous to that described above.

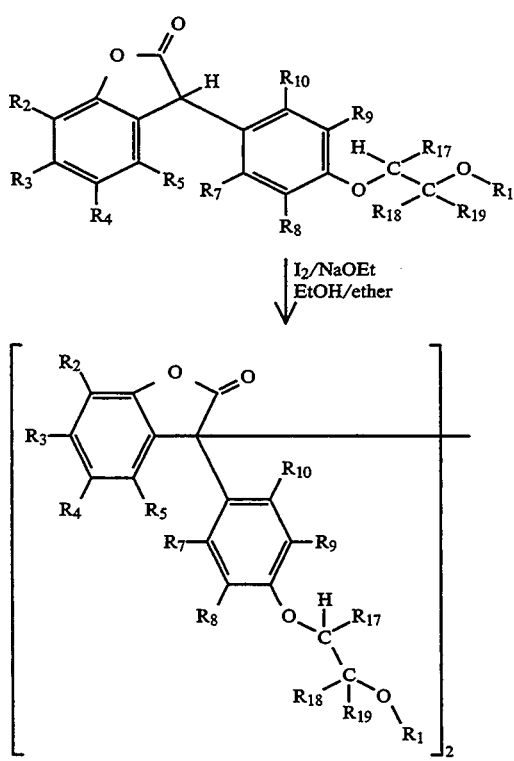

Dimerization of the compounds of the formula (14) for preparing compounds of the formula (1), in which $R_6$ is a group of the formula (3) [compounds of the formula (15)] is effected by oxidation with, for example, iodine under basic conditions in an organic solvent at room temperature. A suitable base is in particular sodium ethoxide, and a suitable solvent is ethanol and diethyl ether.

The compounds according to the invention of the formula (1) are suitable for stabilizing organic materials against thermal, oxidative or light-induced degradation.

Examples of such materials are:

1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), low density polyethylene (LDPE), linear low density polyethylene (LLDPE), branched low density polyethylene (BLDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either $\pi$- or $\sigma$-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals beeing elements of groups Ia, IIa and/or IIIa of the Periodic Table. The activators may be modified conveniently with further ester, ether, amine or silyl ether groups. These catalyst stystems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE./HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example C$_5$–C$_9$) including hydrogenated modifications thereof (e.g. tackifiers) and mixtures of polyalkylenes and starch.

5. Polystyrene, poly(p-methylstyrene), poly(α-methylstyrene).

6. Copolymers of styrene or α-methylstyrene with dienes or acrylic derivatives, for example styrene/butadiene, styrene/acrylonitrile, styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

7. Graft copolymers of styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from α,β-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS.

19. Polycarbonates and polyester carbonates.

20. Polysulfones, polyether sulfones and polyether ketones.

21. Crosslinked polymers derived from aldehydes on the one hand and phenols, ureas and melamines on the other hand, such as phenol/formaldehyde resins, urea/formaldehyde resins and melamine/formaldehyde resins.

22. Drying and non-drying alkyd resins.

23. Unsaturated polyester resins derived from copolyesters of saturated and unsaturated dicarboxylic acids with polyhydric alcohols and vinyl compounds as crosslinking agents, and also halogen-containing modifications thereof of low flammability.

24. Crosslinkable acrylic resins derived from substituted acrylates, for example epoxy acrylates, urethane acrylates or polyester acrylates.
25. Alkyd resins, polyester resins and acrylate resins crosslinked with melamine resins, urea resins, polyisocyanates or epoxy resins.
26. Crosslinked epoxy resins derived from polyepoxides, for example from bisglycidyl ethers or from cycloaliphatic diepoxides.
27. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.
28. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO.
29. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates), red also mixtures of synthetic esters with mineral oils in any weight ratios, typically those used as spinning compositions, as well as aqueous emulsions of such materials.
30. Aqueous emulsions of natural or synthetic rubber, e.g. natural latex or latices of carboxylated styrene/butadiene copolymers.

Accordingly, the invention also provides compositions comprising an organic material subject to oxidative, thermal or light-induced degradation and at least one compound of the formula (1).

Preferred organic materials are polymers, for example synthetic polymers, in particular thermoplastic polymers. Particular preference is given to polyacetals or polyolefins, for example polypropylene or polyethylene.

The action of the compounds according to the invention against thermal and oxidative degradation, in particular in the case of thermal stress, such as occurs during processing of thermoplastics, may be mentioned in particular. The compounds according to the invention are therefore highly suitable for use as processing stabilizers.

Preferably, the compounds of the formula (1) are added to the material to be stabilized in amounts of 0.0005 to 5%, in particular 0.001 to 2%, for example 0.01 to 2%, relative to the weight of the organic material to be stabilized.

As well as the compounds of the formula (1), further costabilizers, such as the following, can be present in the compositions according to the invention:

1. Antioxidants 1.1. Alkylated monophenols, for example 2,6-di-tert-butyl-4-methylphenol, 2-tert-butyl4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, 2,6-di-nonyl-4-methylphenol, 2,4-dimethyl-6-(1'-methylundec-1'-yl)phenol, 2,4-dimethyl-6-(1'-methylheptadec-1'-yl)phenol, 2,4-dimethyl-6-(1'-methyltridec-1'-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis-(3,5-di-tert-butyl-4-hydroxyphenyl) adipate.

1.4. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-3-methylphenol), 4,4'-thiobis-(3,6-di-sec-amylphenol), 4,4'-bis-(2,6-dimethyl-4-hydroxyphenyl) disulfide.

1.5. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)-phenol],2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert -butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-ten-butyl-4'-hydroxyphenyl)butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane 2,2-bis-(3,5-di-tert-butyl-4-hydroxyphenyl)propane, 2,2-bis-(5-tert-butyl-4-hydroxy2-methylphenyl)-4-n-dodecylmercaptobutane, 1,1,5,5-tetra-(5-tert -butyl-4-hydroxy-2-methylphenyl)-pentane.

1.6. O-, N- and S-benzyl compounds, for example 3,5,3',5'-tetra-tert-butyl-4,4'-dihydroxydibenzyl ether, octadecyl-4-hydroxy-3,5-dimethylbenzylmercaptoacetate, tris-(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)-sulfide, isooctyl-3,5di-tert-butyl-4-hydroxybenzylmercaptoacetate.

1.7. Hydroxybenzylated malonates, for example dioctadecyl-2,2-bis-(3,5-di-tert-butyl-2-hydroxybenzyl)-malonate, di-octadecyl-2-(3-tert-butyl-4-hydroxy-5-methylbenzyl)-malonate, di-dodecylmercaptoethyl-2,2-bis-(3,5-di-tert-butyl-4-hydroxybenzyl)malonate, bis[4-(1,1,3,3-tetramethylbutyl)phenyl]-2,2-bis(3,5-di-tert-butyl-4-hydroxybenzyl)malonate.

1.8. Aromatic hydroxybenzyl compounds, for example 1,3,5-tris-(3,5-di-tert-butyl-4-hydroxybenzyl)-2,4,6- trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.9. Triazine Compounds, for example 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris-(3,5-di-tert-butyl-4-hydroxybenzyl)isocyanurate, 1,3,5-tris(4-tert-butyl-3-hydroxy-2,6-dimethylbenzyl)isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.10. Benzylphosphonates, for example dimethyl-2,5-di-tert-butyl-4-hydroxybenzylphosphonate, diethyl-3,5-di-ten-butyl-4-hydroxybenzylphosphonate, dioctadecyl3,5-di-tert-butyl-4-hydroxybenzylphosphonate, dioctadecyl-5-tert-butyl-4-hydroxy3-methylbenzylphosphonate, the calcium salt of the monoethyl ester of 3,5-di-tert-butyl-4-hydroxybenzylphosphonic acid.

1.11. Acylaminophenols, for example 4-hydroxylauranilide, 4-hydroxystearanilide, octyl N-(3,5-di-tert-butyl-4-hydroxyphenyl)carbamate.

1.12. Esters of β-(3,5-di-tert-butyl-4-hydroxyphenyl)propionic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.21-octane.

1.13. Esters of β-(5-tert-butyl-4-hydroxy-3-methylphenyl)propionic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.21]octane.

1.14 Esters of β-(3,5-dicyclohexal-4-hydroxyphenyl)propionic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.21]octane.

1.15 Esters of 3,5-di-tert-butyl-4-hydroxyphenyl acetic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2 ]octane.

1.16. Amides of β-(3,5-di-tert-butyl-4-hydroxyphenyl)propionic acid e.g. N,N'-bis(3,5-di-tert-butyl-4-hydroxyphenylpropionyl)hexamethylenediamine, N,N'-bis(3,5-di-tert-butyl-4-hydroxyphenylpropionyl)-trimethylenediamine, N,N'-bis(3,5-di-tert-butyl-4-hydroxyphenylpropionyl)hydrazine.

2. UV absorbers and light stabilisers 2.1.2-(2'-Hydroxyphenyl)benzotriazoles, for example 2'-(2-hydroxy-5'-methylphenyl)benzotriazole, 2-(3',5'-di-tert-butyl-2'-hydroxyphenyl)benzotriazole, 2-(5-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'-hydroxyphenyl)benzotriazole, 2-(2'-hydroxy-4'-octyloxyphenyl)benzotriazole, 2-(3',5'-di-tert-amyl-2'-hydroxyphenyl)benzotriazole, 2-(3',5'-bis-(α,α-dimethylbenzyl)-2'-hydroxyphenyl)benzotriazole, mixture of 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl)phenyl)-5-chloro-benzotriazole, 2-(3'-tert-butyl-2'-hydroxy-5'-(2-methoxycarbonylcarbonylethyl)phenyl)benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl]-2'-hydroxyphenyl)benzotriazole, 2-(3'-dodecyl-2'-hydroxy-5'-methylphenyl)benzotriazole, and 2-(3'-tert-butyl-2'-hydroxy-5'-(2-isooctyloxycarbonylethyl)phenylbenzotriazole, 2,2'-methylene-bis[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300; [R—CH$_2$CH$_2$—COO(CH$_2$)$_3$]$_2$, where R=3'-tert-butyl-4'-hydroxy-5'-2H-benzotriazol-2-ylphenyl.

2.2.2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, as for example 4-tertbutylphenyl salicylate, phenyl salicylate, octylphenyl salicylate, dibenzoyl resorcinol, bis(4-tert-butylbenzoyl) resorcinol, benzoyl resorcinol, 2,4-di-tertbutylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxy-cinnamate, butyl α-cyano-β-methyl-p-methoxy-cinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thio-bis-[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenyl undecylketoxime, nickel complexes of 1-phenyl-4-lauroyl-5-hydroxypyrazole, with or without additional ligands.

2.6. Sterically hindered amines, for example bis(2,2,6,6-tetramethyl-piperidyl)sebacate, bis(2,2,6,6-tetramethyl-piperidyl)succinate, bis(1,2,2,6,6-pentamethylpiperidyl)sebacate, bis(1,2,2,6,6-pentamethylpiperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, the condensate of N,N'-bis(2,2,6,6-tetramethyl-4-piperidyl)-hexamethylenediamine and 4-tert-octylamino-2,6-dichloro-1,3,5-triazine, tris(2,2,6,6-tetramethyl-4-piperidyl)nitrilotriacetate, tetrakis(2,2,6,6-tetramethyl-4-piperidyl)-1,2,3,4-butane-tetracarboxylate, 1,1'-(1,2-ethanediyl)bis(3,3,5,5-tetramethylpiperinone), 4-benzoyl-2,2,6,6-tetramethylpiperidine, 4-stearyloxy-2,2,6,6-tetramethylpiperidine, bis(1,2,2,6,6-pentamethyl-piperidyl)-2-n-butyl-2-(2-hydroxy-3,5-di-tert-butylbenzyl)malonate, 3-n-octyl-7,7,9,9-tetramethyl-1,3,8-triazasprio[4.5]decan-2,4-dion, bis(1-octyloxy-2,2,6,6-tetramethylpiperidyl)sebacate, bis(1-octyloxy-2,2,6,6-tetramethylpiperidyl)succinate, the condensate of N,N'-bis-(2,2,6,6-tetramethyl-4-piperidyl)hexamethylenediamine and 4-morpholino-2,6-dichloro-1,3,5-triazine, the condensate of 2-chloro-4,6-bis(4-n-butylamino-2,2,6,6-tetramethylpiperidyl)-1,3,5-triazine and 1,2-bis(1,2-bis(3-aminopropylamino)ethane the condensate of 2-chloro-4,6-di-(4-n-butylamino-1,2,2,6,6-pentamethyl-piperidyl)-1,3,5-triazine and 1,2-bis-(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidin-2,5-dione, 3-dodecyl-1-(1,2,2,6,6-pentamethyl-4-piperidyl)pyrrolidine-2,5-dione.

2.7. Oxamides, for example 4,4'-dioctyloxyoxanilide, 2,2'-dioctyloxy-5,5'-di-tert-butoxanilide, 2,2'-didodecyloxy-5,5'-di-tert-butoxanilide, 2-ethoxy-2'-ethoxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide and mixtures of ortho- and para-methoxy-disubstituted oxanilides and mixtures of o- and p-ethoxy-disubstituted oxanilides.

2.8.2-(2-Hydroxyphenyl)-1,3,5-triazines, for example 2,4,6-tris(2-hydroxy-4-octyloxy-phenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2(2-hydroxy -4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-[2-hydroxy-4-(2hydroxy-3-butyloxy-propoxy)phenyl]-4,6-bis(2,4-dimethyl)-1,3,5-triazine, 2-[2-hydroxy-4-(2-hydroxy-3-octyloxy-propyloxy)phenyl]-4,6-bis(2,4-dimethyl)-1,3,5-triazine.

3. Metal deactivators, for example N,N'-diphenyloxamide, N-salicylal-N'-salicyloyl hydrazine, N,N'-bis(salicyloyl) hydrazine, N,N'-bis(3,5-di-tert-butyl-4-hydroxyphenylpropionyl)hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl)oxalyl dihydrazide, N,N'-bis(salicyloyl)thiopropionyl dihydrazide.

4. Phosphites and phosphonites., for example triphenyl phosphite, diphenyl alkyl phosphites, phenyl dialkyl phosphites, tris(nonylphenyl)phosphite, trilauryl phosphite, trioctadecyl phosphite, distearyl pentaerythritol diphosphite, tris(2,4-di-tert-butylphenyl)-phosphite, diisodecyl pentaerythritol diphosphite, bis(2,4-di-tert-butylphenyl)pentaerythritol diphosphite, bis(2,6-di-tert-butyl-4-methylphenyl)-pentaeryt hritol diphosphite, diisodecyloxypentaerythritol diphosphite, bis(2,4-di-tert-butyl-6-methylphenyl)pentaerythritol diphosphite, bis(2,4,6-tris(tert-butylphenyl)pentacrythritol diphsophite, tristearyl sorbitol triphosphite, tetrakis(2,4-di-tert-butylphenyl) 4,4'-biphenylene diphosphonite, 6-isooctyloxy -2,4,8,10-tetra-tert-butyl-12H-dibenz[d,g]-1,3,2-dioxaphosphocin, 6-fluoro-2,4,8,10-tetra-tert-butyl-12-methyl-dibenz[d,g]-1,3,2-dioxaphosphocin, bis(2,4-di-tert-butyl-6-methylphenyl)methylphosphite, bis(2,4-di-tert-butyl-6-methylphenyl)ethylphosphite.

5. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

6. Polyamide stabilisers, for example, copper salts in combination with iodides and/or phosphorus compounds and salts of divalent manganese.

7. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example calcium stearate, zinc stearate, magnesium behenate, magnesium stearate, sodium ricinoleate and potassium palmitate, antimony pyrocatecholate or tin pyrocatecholate.

8. Nucleating agents, for example, 4-tert-butylbenzoic acid, adipic acid, diphenylacetic acid.

9. Fillers and reinforcing agents, for example, calcium carbonate, silicates, glass fibres, asbestos, talc, kaolin, mica, barium sulfate, metal oxides and hydroxides, carbon black, graphite.

10. Other additives, for example, plasticisers, lubricants, emulsifiers, pigments, optical brighteners, flameproofing agents, antistatic agents and blowing agents.

The costabilizers are added, for example, in concentrations of 0.01 to 10%, relative to the total weight of the material to be stabilized.

The compounds according to the invention of the formula (1) can be used in particular together with phenolic antioxidants. Accordingly, the compositions according to the invention preferably contain, apart from the compounds of the formula (1), phenolic antioxidants, in particular those listed under above items 1.1 to 1.16.

Other preferred compositions contain at least one organic phosphite or phosphonite in addition to the compounds of the formula (1).

Incorporation of the compounds of the formula (1) and, if desired, further additives in the polymeric, organic material takes place by known methods, for example before or during moulding or else by applying the dissolved or dispersed compounds to the polymeric, organic material, if appropriate with subsequent evaporation of the solvent. The compounds of the formula (1) can also be added to the materials to be stabilized in the form of a masterbatch which contains these compounds, for example, in a concentration of 2.5 to 25% by weight.

The compounds of the formula (1) can also be added before or during polymerization or before crosslinking.

The compounds of the formula (1) can be incorporated in the material to be stabilized in pure form or encapsulated in waxes, oils or polymers.

The compounds of the formula (1) can also be sprayed onto the polymer to be stabilized. They are capable of diluting other additives (for example the abovementioned customary additives) or their melts, thus enabling them also to be sprayed onto the polymer to be stabilized together with these additives. A particularly advantageous method is the addition by spraying during deactivation of the polymerization catalyst, it being possible, for example, for the steam used for deactivation to be used for spraying.

In the case of bead-polymerized polyolefins, it may be advantageous, for example, to apply the compounds of the formula (1), if appropriate together with other additives, by spraying.

Accordingly, a preferred embodiment of the present invention is the use of compounds of the formula (1) for stabilizing organic materials against oxidative, thermal or light-induced degradation.

The materials thus stabilized can be used in a variety of forms, for example as films, fibres, ribbons, moulding compositions, profiles or binders for coatings and paints, adhesives or cements.

The present invention also provides a process for stabilizing an organic material against oxidative, thermal or light-induced degradation, which comprises incorporating therein or applying thereto at least one compound of the formula (1).

As already pointed out, the compounds according to the invention are particularly advantageously used as stabilizers in polyolefins, in particular as heat stabilizers. Excellent stabilization is obtained, for example, in those cases where they are used in combination with organic phosphites or phosphonites. In these combinations, the compounds according to the invention have the advantage that they are effective even in extremely small amounts. They are used, for example, in amounts of 0.0001 to 0.015, in particular 0.0001 to 0.008% by weight, relative to the polyolefin. The organic phosphite or phosphonite is advantageously used in an amount of 0.01 to 2, in particular 0.01 to 1% by weight, also relative to the polyolefin. The organic phosphites or phosphonites preferably used are those described in DE-A-4 202 276. In this publication, see, in particular, the claims, the examples and page 5, last paragraph to page 8. Particularly advantageous phosphites and phosphonites can also be seen from item 4 of the above list of costabilizers.

The examples which follow further illustrate the invention. The parts and percentages given are by weight.

EXAMPLE 1

Preparation of 3-[4-(2-acetoxyethoxy)phenyl]-5,7-di-tert-butylbenzofuran2-one (compound (101), Table 1).

A suspension of 154.7 g (0.75 mol) of 2,4-di-tert-butylphenol and 106.1 g (0.50 mol) of 4-(2-hydroxyethoxy)-mandelic acid (compound (201), Example 10, Table 2) in 200 ml of acetic acid saturated with hydrogen chloride gas stirred under a nitrogen atmosphere is refluxed for 8 hours. The acetic acid is then distilled off on a vacuum rotary evaporator, 15 ml (0.21 mol) of acetyl chloride are added to the residue, and the mixture is maintained at 120° C. for 20 minutes. The reaction mixture is again concentrated on a vacuum rotary evaporator, 400 ml of methanol are added to the residue, and the mixture is allowed to stand at about −8° C. The precipitated crystals are filtered off, washed with 250 ml of cold methanol and dried to give 176.3 g (83%) of 3-[4-(2-acetoxyethoxy)phenyl]-5,7-di-tert-butylbenzofuran-2-one, m.p. 93°–96° C. (compound (101), Table 1). Recrystallization from ligroin yields the compound (101) in two crystal forms. Crystal form A: m.p. 75°–78° C., enthalpy of fusion 62.4 Joule/g. Crystal form B: m.p. 93°–96° C., enthalpy of fusion 118.2 Joule/g.

Analogously to Example 1, the compounds (102), (103), (104), (112), (118), (123), (127), (128), (136), (137), (138), (139) and (140) are prepared from the corresponding phenols (for example 4-tert-butyl-phenol, 1-naphthol, 2-(hexadec-2-yl)-4-tert-butylphenol or 2,4-dicyclohexyl-phenol), mandelic acids (Examples 10 and 11), carboxylic acid solvents (for example formic acid, acetic acid or propionic acid) and acid chlorides (see Table 1). Compound (123) is prepared in formic acid instead of acetic acid without addition of an acid chloride.

EXAMPLE 2

Preparation of 3-[4-(2-hydroxyethoxy)phenyl]-5-methyl-benzofuran-2-one (compound (119), Table 1).

A suspension of 8.5 g (40.0 mmol) of 4-(2-hydroxyethoxy)mandelic acid (compound (201), Example 10, Table 2) and 12.0 g (110 mmol) of p-cresol is maintained at 180° C. under a nitrogen atmosphere for 75 minutes, during which the water formed distils off. Excess p-cresol is then distilled off in a vacuum rotary evaporator. Chromatography of the residue on silica gel using the eluent system 9:1 dichloromethane/ethyl acetate gives 6.6 g (58%) of 3-[4-(2-hydroxyethoxy)phenyl]-5-methylbenzofuran-2-one, a yellowish resin (compound (119), Table 1).

Analogously to Example 2, the compounds (113) and (114) are prepared from the corresponding phenols and mandelic acids (Example 12) (see Table 1).

EXAMPLE 3

Preparation of 5,7-di-tert-butyl-3-[4-(2-hydroxyethoxy)phenyl]-benzofuran-2-one (compound (105), Table 1).

a) By hydrolysis of 3-[4-(2-acetoxyethoxy)phenyl]-5,7-di-tert-butyl-benzofuran-2-one (Example 1, compound (101), Table 1).

A solution of 170 g (0.40 tool) of 3-[4-(2-acetoxyethoxy)phenyl]-5,7-di-tert-butylbenzofuran-2-one (Example 1) in 1000 ml of methanol and 40 ml of concentrated hydrochloric acid is refluxed for 15 hours. The reaction mixture is then concentrated by distilling off about 600 ml of methanol, and the resulting mixture is allowed to stand in a refrigerator. The precipitated crystals are filtered off, washed with 200 ml of cold methanol and dried to give 137.5 g (90%) of 5,7-di-tert-butyl-3-[4-(2-hydroxyethoxy)phenylbenzofuran-2one, m.p. 132°–135° C. (compound (105), Table 1).

Analogously to Example 3a, 5,7-di-tert-butyl-3-[3,5-dimethyl-4-(2-hydroxyethoxy)phe-nyllbenzofuran-2-one (compound (106), Table 1) is prepared from compound (104) (Example 1).

b) By hydroxyethylation of 5,7-di-tert-butyl-3-(4-hydroxyphenyl)benzofuran-2-one.

1.0 ml (15.0 mmol) of 2-chloroethanol is added to a solution of 3.38 g (10.0 mmol) of 5,7-di-tert-butyl-3-(4-hydroxyphenyl)benzofuran-2-one in 30 ml of 1N sodium hydroxide solution heated to 80° C. The reaction mixture is then maintained at 80° C. for 2 hours, 50 ml of 1N hydrochloric acid are added, stirring is continued for 1 hour, the mixture is cooled, and the product is extracted with dichloromethane. The organic phases are washed with water, combined, dried over sodium sulfate and concentrated on a vacuum rotary evaporator. Crystallization of the residue from 8 ml of ethanol and 2 ml of water gives 2.34 g (61%) of 5,7-di-tert-butyl-3-[4-(2-hydroxyethoxy)phenyl]-benzofuran-2-one m.p. 132°–135° C. (compound (105), Table 1).

The 5,7-di-tert-butyl-3-(4-hydroxyphenyl)benzofuran-2-one required as starting material is prepared as follows:

A mixture of 103.2 g (0.50 mol) of 2,4-di-tert-butyl-phenol and 102.4 g (0.55 mol) of 4-hydroxymandelic acid monohydrate in 100 ml of acetic acid is refluxed under a nitrogen atmosphere for 24 hours. The reaction mixture is then diluted with 140 ml of 50% aqueous acetic acid, cooled, and the precipitate formed is filtered off. The residue is washed with a further 200 ml of 50% aqueous acetic acid and then dried to give 95.9 g (57%) of 5,7-di-tert-butyl-3-(4-hydroxyphenyl)benzofuran-2-one, m.p. 187°–190° C.

EXAMPLE 4

Preparation of 5,7-di-tert-butyl-3-[4-(2-stearoyloxyethoxy)phenyl]-benzofuran -2-one (compound (107), Table 1).

A suspension of 11.4 g (30 mmol) of 5,7-di-tert-butyl-3-[4-(2-hydroxyethoxy)phenyl]ben-zofuran-2-one (compound (105), Example 3) and 9.4 g (31 mmol) of stearoyl chloride in 60 ml of toluene is refluxed for 4 hours. The reaction mixture is then concentrated on a vacuum rotary evaporator, and the residue is recrystallized from methanol to give 17.3 g (89%) of 5,7-di-tert-butyl-3-[4-(2-stearoyloxyethoxy)phenyl]benzofuran-2-one, m.p. 54°–60° C. (compound (107), Table 1).

Analogously to Example 4, the compounds (108), (121), (122), (124), (125), (133), (134) and (141) are prepared from the corresponding benzofuranones and acid chlorides.

EXAMPLE 5

Preparation of the terephthalic ester derivative (compound (111), Table 1).

A suspension of 4.0 g (20 mmol) of dimethyl terephthalate, 16.0 g (42 mmol) of 5,7-di-tert-butyl-3-[4-(2-hydroxyethoxy)phenyl]-benzofuran-2-one (compound (105), Example 3) and 300 mg of dibutyltin oxide is stirred under nitrogen at 170° C. for 30 minutes, during which the methanol formed distils off. The temperature is then increased to 240° C., and stirring is continued for another 1.5 hours under a slight vacuum (50 mbar). After removal of the heating bath, 20 ml of chlorobenzene and then 75 ml of isopropanol are poured to the melt via the condenser. The reaction mixture is cooled with ice/water. The precipitated product is filtered off, washed with cold isopropanol and dried to give 15.6 g (87%) of the compound (111) (Table 1), m.p. 248°–251° C.

Analogously to Example 5, the compounds (109), (110), (115), (117), (120), (142), (143) and (144) are prepared from the corresponding esters and benzofuranones.

EXAMPLE 6

Preparation of the succinic ester derivative (compound (116), Table 1).

A suspension of 7.65 g (20.0 mmol) of 5,7-di-tert-butyl-3-[4-(2-hydroxyethoxy)phenyl]-benzofuran-2-one (compound (105), Example 3), 1.0 g (10.0 mmol) of succinic anhydride and 1 drop of methanesulfonic acid is maintained at 150° C. under nitrogen atmosphere for 30 minutes. Stirring at 150° C. is then continued for another 2 hours under a slight vacuum (50 mbar). The reaction mixture is cooled and chromatographed on silica gel using the eluent system 19:1 dichloromethane/hexane. Crystallization of the pure fractions from ethanol gives 6.5 g (77%) of the compound (116) (Table 1), m.p. 145°–163° C.

Analogously to Example 6, the compound (131) is prepared from thiodipropionic acid instead of succinic anhydride as the starting material.

EXAMPLE 7

Preparation of 5,7-di-tert-butyl-3-[4-(2-methylaminocarboxyethoxy)-phenyl]-benzofuran-2-one (compound (129), Table 1).

A suspension of 3.83 g (10.0 mmol) of 5,7-di-tert-butyl-3[4-(2-hydroxyethoxy)phenyl]-benzofuran-2-one (compound (105), Example 3), 0.60 ml (10.0 mmol) of methyl isocyanate and 100 mg of dibutyltin oxide is stirred at room temperature for 3 hours and then concentrated on a vacuum rotary evaporator. Crystallization of the residue from 10 ml of ethanol gives 2.3 g (52%) of 5,7-di-tert-butyl-3-[4-(2-methylaminocarboxyethoxy)phenyl]-benzofuran-2-one, m.p. 115°–121° C. (compound (129), Table 1).

Analogously to Example 7, the compound (132) is prepared from half an equivalent of hexamethylene diisocyanate instead of methyl isocyanate as the starting material.

EXAMPLE 8

Preparation of the compound (130), (Table 1).

A suspension of 11.5 g (30.0 mmol) of 5,7-di-tert-butyl-3-[4-(2-hydroxyethoxy)phenyl]-benzofuran-2-one (compound (105), Example 3), 5.3 ml (90.0 mmol) of methylisocyanate and 200 mg of dibutyltin oxide in 25 ml of toluene are refluxed for 30 minutes. The reaction mixture is then concentrated on a vacuum rotary evaporator. The residue is recrystallized twice from 25 ml of methanol each time to give 8.9 g (59%) of the compound (130), m.p. 142°–144° C.

Example 9

Preparation of 3,3'-bis-[5,7-di-tert-butyl-3-(4-[2-hydroxyethoxy]-phenyl)-benzofuran-2-one] (compound (135), Table 1).

11.48 g (50 mmol) of 5,7-di-tert-butyl-3-[4-(2-hydroxyethoxy)phenyl]benzofuran-2-one (compound (105), Example 3) are added under a nitrogen atmosphere to a sodium ethoxide solution prepared by addition of 0.69 g (30.0 mmol) of sodium to 40 ml of absolute ethanol. A solution of 3.8 g (15.0 mmol) of iodine in 40 ml of diethyl ether is then added dropwise at room temperature over a period of about 10 minutes. The reaction mixture is stirred for another 30 minutes, then diluted with 200 ml of water and extracted three times with 50 ml each of diethyl ether. The organic phases are separated off, washed with water, combined, dried over magnesium sulfate and concentrated on a vacuum rotary evaporator. Crystallization of the residue from ligroin/dichloromethane gives 10.3 g (90%) of 3,3'-bis-[5,7-di-tert-butyl-3-(4-[2-hydroxyethoxy]phenyl)-benzofuran-2-one], m.p. 212°-218° C. (compound (135), Table 1).

The structural abbreviation of the formulae in Table 1 and 2, for example

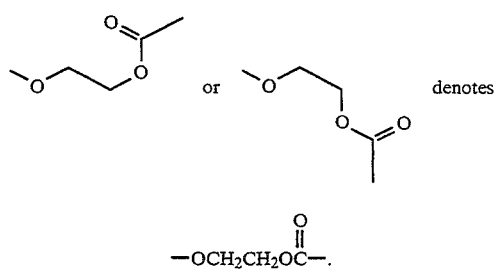

denotes —OCH₂CH₂OC—.

$$-OCH_2CH_2OC\overset{O}{\underset{\|}{C}}-$$

TABLE 1

| No. | Compound | m.p. (°C.) | C(%), H(%) (calculated/found) | | Yield (%) |
|---|---|---|---|---|---|
| 101 | [structure] | 93–96 | 73.56 73.54 | 7.60 7.60 | 83 |
| 102 | [structure] | 55–60 | 73.95 73.84 | 7.81 7.88 | 87 |
| 103 | [structure] | 124–128 | 73.95 73.84 | 7.81 7.82 | 70 |
| 104 | [structure] | 86–92 | 74.31 74.26 | 8.02 8.16 | 49 |
| 105 | [structure] | 132–135 | 75.36 75.05 | 7.91 7.90 | 90 |

TABLE 1-continued

| # | Structure | mp (°C) | C% found/calc | H% found/calc | Yield % |
|---|---|---|---|---|---|
| 106 | [structure: 3,5-di-tert-butyl-2-hydroxyphenyl / 3,5-dimethyl-4-(2-hydroxyethoxy)phenyl acetate] | resin | 76.06 / 76.00 | 8.35 / 8.35 | ~100 |
| 107 | [structure: 3,5-di-tert-butyl-2-hydroxyphenyl / 4-(2-stearoyloxyethoxy)phenyl acetate] | 54–60 | 77.73 / 77.75 | 9.94 / 9.96 | 89 |
| 108 | [structure: 3,5-di-tert-butyl-2-hydroxyphenyl / 3,5-dimethyl-4-(2-stearoyloxyethoxy)phenyl acetate] | resin | 78.06 / 78.11 | 10.12 / 10.16 | 80 |
| 109 | [structure: bis ester, (CH₂)₂ linker] | 130–142 | 74.12 / 74.02 Mixture of diastereomers | 7.60 / 7.67 | 58 |
| 110 | [structure: bis ester, (CH₂)₄ linker] | resin | Characterized by ¹H NMR(CDCl₃) δ(H*) = 4.78 ppm Mixture of diastereomers | | 47 |

TABLE 1-continued
| 111 | 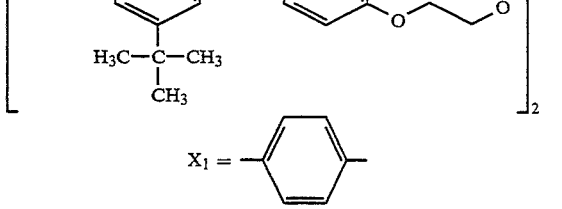 | 248–251 | 75.14 6.98<br>75.04 7.04<br>Mixture of<br>diastereomers | 87 |
| --- | --- | --- | --- | --- |
| 112 | 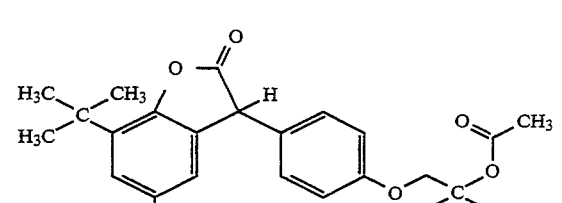 | resin | 74.31 8.02<br>74.29 8.12<br>Mixture of<br>diastereomers | 32 |
| 113 | 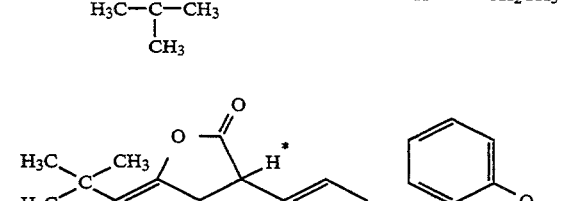 | resin | Characterized by<br>$^1$H NMR(CDCl$_3$)<br>δ(H*) = 4.78 ppm<br>Mixture of<br>diasteromers | 43 |
| 114 | 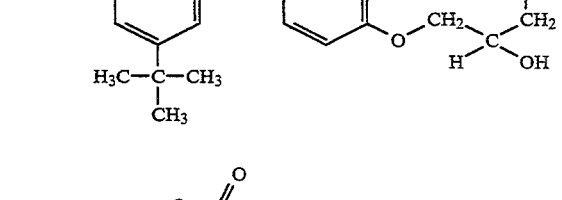 | resin | 74.33 8.60<br>74.28 8.58<br>Mixture of<br>diastereomers | 23 |
| 115 | 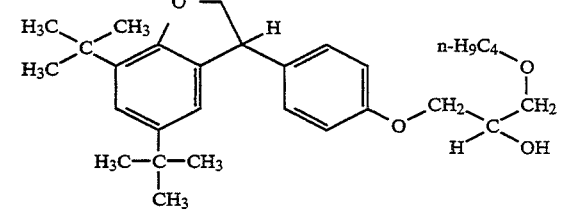 | 137–140 | 76.60 8.47<br>76.59 8.50 | 65 |

TABLE 1-continued

| # | Structure | mp (°C) | Analysis C | Analysis H | Yield |
|---|---|---|---|---|---|
| 116 | (structure with di-tert-butyl phenol, phenyl, ethoxy ester, bracketed ×2) | 145–163 | 73.73 / 73.70 | 7.38 / 7.40 Mixture of diastereomers | 77 |
| 117 | (structure with di-tert-butyl phenol, phenyl, ethoxy ester –X₃; X₃ = —CH₂CH₂—(3-methyl-5-tert-butyl-4-hydroxyphenyl)) | 127–129 | 75.97 / 76.01 | 8.05 / 8.00 | 75 |
| 118 | (structure with mono-tert-butyl phenol, phenyl, ethoxyacetate) | 98–100 | 71.72 / 71.53 | 6.57 / 6.71 | 43 |
| 119 | (structure with methyl phenol, phenyl, ethoxy-OH, H*) | resin | Characterized by $^1$H NMR(CDCl$_3$) δ(H*) = 4.79 ppm | | 58 |
| 120 | (structure with methyl phenol, phenyl, ethoxy ester-CH₂-P(O)(OCH₂CH₃)₂, H*) | resin | Characterized by $^1$H NMR(CDCl$_3$) δ(H*) = 4.80 ppm | | 83 |

TABLE 1-continued

| | | | | | |
|---|---|---|---|---|---|
| 121 | (structure) | oil | 76.56<br>76.41 | 9.28<br>9.38 | 86 |
| 122 | (structure) | 102–105 | 74.65<br>74.78 | 8.21<br>8.21 | 91 |
| 123 | (structure) | 85–89 | 73.15<br>73.13 | 7.37<br>7.38 | 45 |
| 124 | (structure) | resin | 75.11<br>75.43 | 9.26<br>8.77 | 81 |
| 125 | (structure) | 54–57 | 77.38<br>77.31 | 9.74<br>9.74 | 88 |

TABLE 1-continued
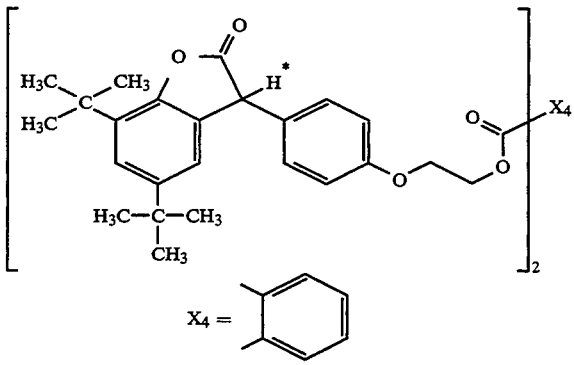

TABLE 1-continued
| No. | Compound | m.p. (°C.) | C(%), H(%) (calculated/found) | | Yield (%) |
|---|---|---|---|---|---|
| 131 | 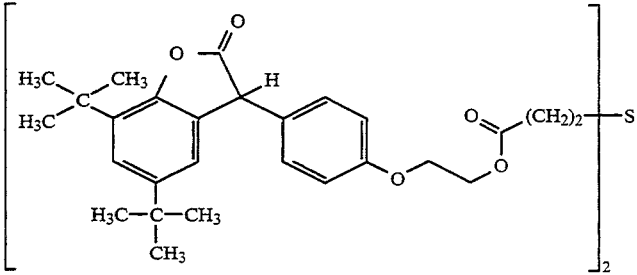 | resin | C(%), H(%), S(%) (calculated/found) 71.50 7.33 3.53 71.28 7.35 3.48 Mixture of diastereomers | | 88 |
| 132 | 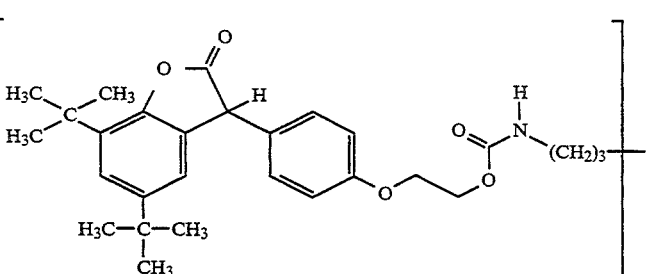 | 67–82 | 72.08 7.78 72.11 7.80 Mixture of diastereomers | | 66 |
| 133 | 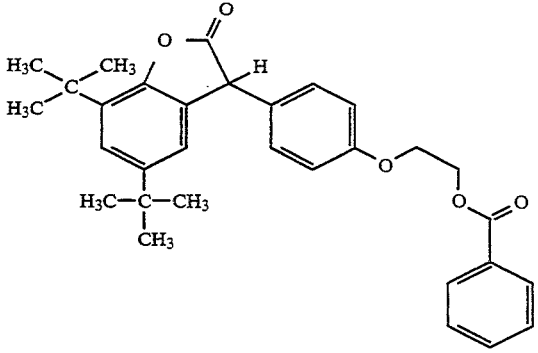 | 127–132 | 76.52 7.04 76.36 7.03 | | 56 |
| 134 | 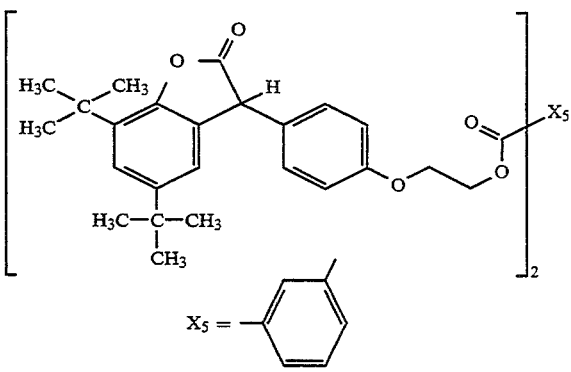  X₅ = | 94–97 | 75.14 6.98 75.95 7.07 Mixture of diastereomers | | 91 |
| 135 | 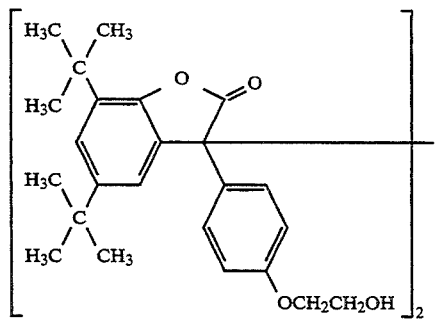 | 212–218 | 75.56 7.66 75.39 7.71 Mixture of diastereomers | | 90 |

TABLE 1-continued
| No. | Compound | m.p. (°C.) | C(%), H(%), S(%) (calculated/found) | Yield (%) |
|---|---|---|---|---|
| 136 | 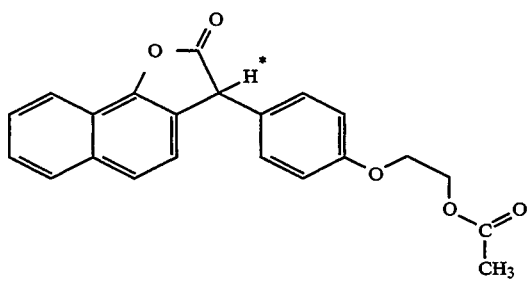 | resin | Characterized by $^1$H NMR(CDCl$_3$) δ(H*) = 5.02 ppm | 69 |
| 137 | 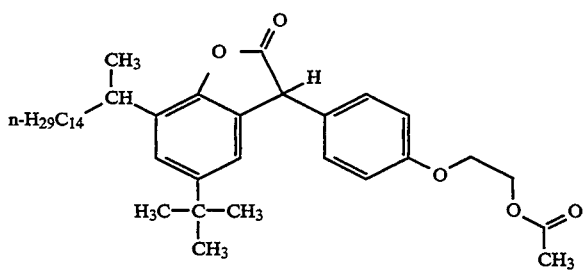 | 68–71 | 76.85 9.67<br>76.64 9.70<br>Mixture of diastereomers | 81 |
| 138 | 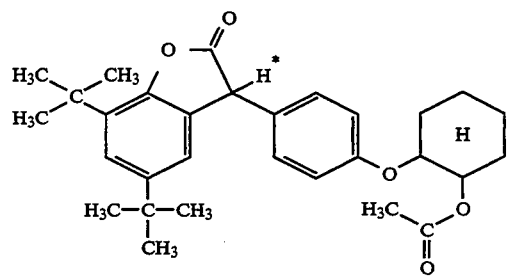 | resin | Characterized by $^1$H NMR(CDCl$_3$) δ(H*) = 4.77 ppm<br>Mixture of diastereomers | 58 |
| 139 | 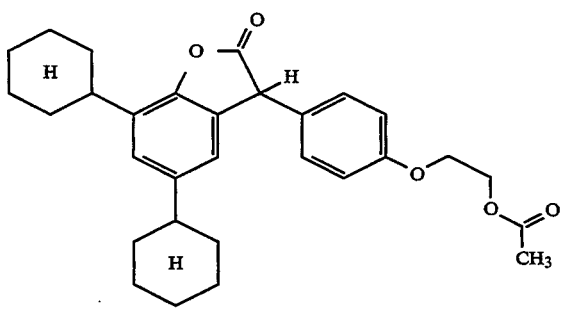 | 88–96 | 75.60 7.61<br>75.53 7.66 | 49 |
| 140 | 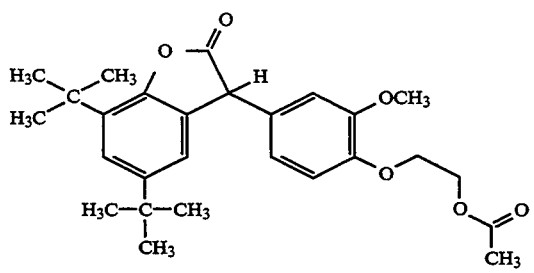 | 94–97 | 71.34 7.54<br>71.26 7.61 | 34 |

TABLE 1-continued

| # | Structure | mp | Analysis | Yield |
|---|---|---|---|---|
| 141 | (structure) | resin | Characterized by $^1$H NMR(CDCl$_3$) δ(H*) = 4.78 ppm | 86 |
| 142 | (structure), $X_6 = -CH_2CH_2-$(3-tert-butyl-4-hydroxyphenyl) | resin | Characterized by $^1$H NMR(CDCl$_3$) δ(H*) = 4.80 ppm | 89 |
| 143 | (structure), $X_7 = -CH_2SCH_2-$(3,5-di-tert-butyl-4-hydroxyphenyl) | resin | 72.96  8.06  4.75 <br> 72.83  8.13  4.75 | 63 |
| 144 | (structure), $X_8 = $ (3,5-di-tert-butyl-4-hydroxyphenyl) | 114–115 | 76.19  8.20 <br> 76.13  8.32 | 50 |

EXAMPLE 10

Preparation of 4-(2-hydroxyethoxy)mandelic acid (compound (201), Table 2).

1040.8 g (5.00 mol) of 4-hydroxymandelic acid, sodium salt monohydrate, 10.0 g (0.25 mol) of sodium hydroxide and 1000 ml of water are placed in an autoclave of 6.3 liter capacity. The autoclave is flushed with nitrogen and 330.4 g (7.50 mol) of ethylene oxide are then injected. The contents are slowly heated to 95° C. over a period of 2 hours with stirring and stirred at this temperature for another 2 hours. The still hot reaction mixture is poured into another vessel, acidified at 95° C. with 540 ml (about 5.5 mol) of 32% hydrochloric acid and crystallized by slow cooling to about +10° C. The precipitated product is filtered with 1000 ml of cold water and dried to give 948 g (89%) of 4-(2-hydroxyethoxy)mandelic acid, m.p. 162°–164° C. (compound (201), Table 2).

Analogously to Example 10, compound (202) (Table 2) is prepared from 3,5-dimethyl-4-hydroxymandelic acid, sodium salt (Example 13) as the starting material. Compounds (206) and (207) (Table 2) are obtained by using propylene oxide or cyclohexene oxide instead of ethylene oxide.

EXAMPLE 11

Preparation of 4-(2-hydroxyethoxy)-3-methylmandelic acid (compound (203), Table 2).

A solution of 8.0 g (200 mmol) of sodium hydroxide in 15 ml of water is added dropwise over a period of one hour to a solution of 18.2 g (100 mmol) of 4-hydroxy-3-methylmandelic acid (Example 13), 4.0 g (100 mmol) of sodium hydroxide and 13.4 ml (200 mmol) of 2-chloroethanol in 60 ml water heated to 70° C. Another 6.7 ml (100 mmol) of 2-chloroethanol and 4.0 g (100 mmol) of sodium hydroxide in 10 ml of water are then added. After another 15 minutes, the reaction mixture is acidified with concentrated hydrochloric acid and extracted twice with ethyl acetate. The organic phases are washed with water, combined, dried over magnesium sulfate and concentrated on a vacuum rotary evaporator. This gives 23.0 g (about 100%) of 4-(2-hydroxyethoxy)-3-methylmandelic acid as a yellowish resin (compound (203), Table 2).

Analogously to Example 11, compound (208) (Table 2) is obtained from 4-hydroxy-3-methoxymandelic acid (Beilstein, 10, IV, 2034) as the starting material.

EXAMPLE 12

Preparation of 4-(2-hydroxy-3-phenoxypropoxy)mandelic acid (compound (204), Table 2).

7.5 g (50 mmol) of 2,3-epoxypropyl phenyl ether (phenyl glycidyl ether) are added to a suspension of 10.4 g (50 mmol) of 4-hydroxymandelic acid sodium salt monohydrate, and 300 mg (5.0 mmol) of potassium hydroxide in 25 ml of methanol, and the mixture is refluxed for 8 hours. The homogeneous reaction mixture is then diluted with 300 ml of water, acidified with 25 ml of concentrated hydrochloric acid and extracted three times with dichloromethane. The organic phases are washed with water, combined, dried over magnesium sulfate and concentrated on a vacuum rotary evaporator to give 8.4 g (53%) of 4-(2-hydroxy-3-phenoxypropoxy)mandelic acid as a yellowish resin (compound (204), Table 2).

Analogously to Example 12, compound (205) (Table 2) is obtained from 1,2-butylene oxide instead of 2,3-epoxypropyl phenyl ether as the starting material.

EXAMPLE 13

Preparation of substituted 4-hydroxymandelic acids:

0.30 mol of the starting phenol (for example 2,6-dimethylphenol, o-cresol, 2-tert-butylphenol or 2-isopropyl-3-methylphenol) is dissolved in 150 ml of 2N sodium hydroxide solution under a nitrogen atmosphere. After cooling to +5° C., 4.8 g (0.12 mol) of sodium hydroxide and 13.3 ml (0.12 tool) of 50% aqueous glyoxylic acid are added, and the reaction mixture is stirred at room temperature for 4 hours. After 4 hours each, another 0.12 mol of sodium hydroxide and glyoxylic acid are added twice (a total of 0.36 mol). The reaction mixture is then stirred for another 12 hours, neutralized with concentrated hydrochloric acid and washed twice with 75 ml of petroleum ether. The aqueous phase is then acidified with concentrated hydrochloric acid and extracted several times with ether. The organic phases are combined, dried over magnesium sulfate and concentrated on a vacuum rotary evaporator. In this manner, the following compounds are obtained: 3,5-dimethyl-4-hydroxymandelic acid, m.p. 132°–135° C. (85%); 4-hydroxy-3-methylmandelic acid, m.p. 115°–120° C., yield 55%; 4-hydroxy-3-tert-butylmandelic acid, m.p. 156°–158° C., yield 26% and 3-isopropyl-4-hydroxy-2-methylmandelic acid, m.p. 114°–119° C., yield 20%.

TABLE 2

| No. | Compound | m.p. (°C.) | C(%), H(%) (calculated/found) | | Yield (%) |
|---|---|---|---|---|---|
| 201 | 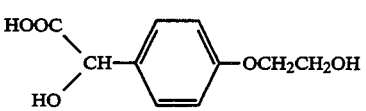 | 162–164 | 56.60 / 56.55 | 5.70 / 5.73 | 89 |
| 202 | 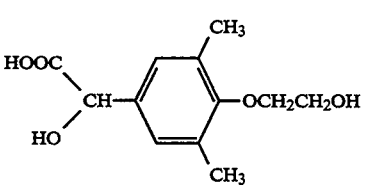 | 145–148 | 59.99 / 60.21 | 6.71 / 6.75 | 57 |

TABLE 2-continued

| No. | Compound | m.p. (°C.) | C(%), H(%) (calculated/found) | Yield (%) |
|---|---|---|---|---|
| 203 | HOOC-CH*(OH)-C6H3(CH3)-OCH2CH2OH | resin | Characterized by $^1$H NMR(DMSO-d$_6$) δ(H*) = 4.91 ppm | ~100 |
| 204 | HOOC-CH*(OH)-C6H4-O-CH2-CH(OH)-CH2-O-C6H5 | resin | Characterized by $^1$H NMR(DMSO-d$_6$) δ(H*) = 4.95 ppm Mixture of diastereomers | 53 |
| 205 | HOOC-CH*(OH)-C6H4-O-CH2-CH(OH)-CH2CH3 | 150–205 | Characterized by $^1$H NMR(DMSO-d$_6$) δ(H*) = 4.83 ppm Mixture of diastereomers | 40 |
| 206 | HOOC-CH*(OH)-C6H4-O-CH2-CH(OH)-CH3 | 138–145 | 58.40  6.24 / 58.27  6.21 Mixture of diastereomers | 71 |
| 207 | HOOC-CH*(OH)-C6H4-O-cyclohexyl(OH) | 150–160 | Characterized by $^1$H NMR(DMSO-d$_6$) δ(H*) = 4.93 ppm Mixture of diastereomers | 69 |
| 208 | HOOC-CH*(OH)-C6H3(OCH3)-OCH2CH2OH | resin | Characterized by $^1$H NMR(DMSO-d$_6$) δ(H*) = 4.94 ppm | 30 |

EXAMPLE 14

Stabilization of polypropylene in multiple extrusion 1.3 kg of polypropylene powder (Profax 6501), which had been prestabilized with 0.025% of Irganox ® 1076 (n-octadecyl 3-[3,5-di-tert-butyl-4-hydroxyphenyl]propionate) (having a melt index as measured at 230° C. and on 2.16 kg of 3.2) are mixed with 0.05% of Irganox ® 1010 (pentaerythritol tetrakis[3-(3,5-di-tert-butyl-4-hydroxyphenyl)propionate], 0.05% of calcium stearate, 0.03% of DHT 4A ® (Kyowa Chemical Industry Co., Ltd., [Mg$_{4.5}$Al$_2$(OH)$_{13}$CO$_3$.3,5 H$_2$O]) and 0.015% of the compound from Table 1. This mixture is extruded in an extruder 20 mm in cylinder diameter and 400 mm in length at 100 revolutions per minute, the 3 heating zones being set at the following temperatures: 260°, 270°, 280° C. For cooling, the extrudate is passed through a waterbath and then granulated. These granules are repeatedly extruded. After 3 extrusions, the melt index is measured (at 230° C. on 2.16 kg). A large increase in the melt index indicates extensive chain degradation, that is poor stabilization. The results are summarized in Table 3.

TABLE 3

| Compound from Table 1 | Melt index after 3 extrusions |
|---|---|
| — | 17.1 |
| 101 | 6.1 |
| 103 | 5.6 |
| 104 | 5.7 |
| 105 | 5.4 |
| 106 | 6.0 |
| 109 | 5.4 |
| 111 | 5.7 |
| 114 | 5.5 |
| 116 | 5.7 |
| 117 | 5.6 |
| 118 | 5.3 |
| — | 17.1 |
| 121 | 5.6 |
| 122 | 5.8 |
| 123 | 5.6 |
| 124 | 5.8 |
| 126 | 6.0 |
| 128 | 5.7 |

TABLE 3-continued

| Compound from Table 1 | Melt index after 3 extrusions |
|---|---|
| 133 | 6.0 |
| 134 | 5.9 |
| 139 | 5.7 |
| 141 | 5.9 |

EXAMPLE 15

Stabilization of polyethylene during processing 100 parts of polyethylene powder (Lupolen® 5260 Z) are mixed with 0.05 part of pentaerythritol tetrakis[3-(3,5-di-tert-butyl-4-hydroxyphenyl)propionate], 0.05 part of tris(2,4-di-tert-butylphenyl)phosphite and 0.05 part of the compound from Table 1, and the mixture is kneaded in a Brabender plastograph at 220° C. and 50 revolutions per minute. During this time, the resistance to kneading is continuously recorded as torque. During the kneading period, the polymer, after remaining unchanged for an extended period of time, starts crosslinking, which can be detected by the rapid increase in torque. In Table 4, the time until the torque markedly increases is listed as a measure of the stabilizing effect. The longer this time, the better the stabilization.

| Compound from Table 1 | Time until the torque increases (min) |
|---|---|
| — | 9.5 |
| 101 | 25.0 |
| 103 | 24.5 |
| 105 | 28.0 |
| 107 | 28.5 |
| 109 | 26.0 |
| 111 | 30.0 |
| 113 | 29.0 |
| 114 | 28.0 |
| 115 | 35.5 |
| 116 | 27.0 |
| 121 | 29.0 |
| 122 | 29.5 |
| — | 9.5 |
| 123 | 29.0 |
| 124 | 27.5 |
| 125 | 26.5 |
| 126 | 28.5 |
| 128 | 25.5 |
| 130 | 26.0 |
| 132 | 25.0 |
| 133 | 28.0 |
| 134 | 29.0 |
| 135 | 27.5 |
| 137 | 27.0 |
| 141 | 27.0 |

What is claimed is:

1. A compound of the formula (1)

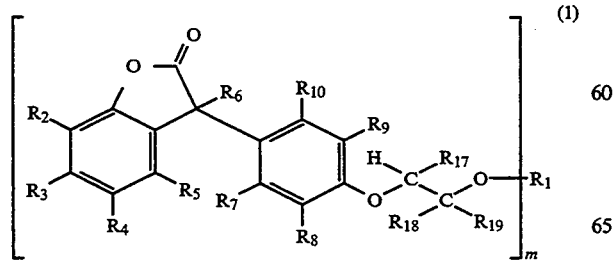

in which, when m is 1, $R_1$ is hydrogen $C_1$-$C_{25}$alkanoyl $C_3$-$C_{25}$alkenoyl $C_3$-$C_{25}$alkanoyl which is interrupted by oxygen, sulfur or

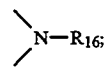

$C_2$-$C_{25}$alkanoyl substituted by a di($C_1$-$C_6$alkyl)-phosphonate group; $C_6$-$C_9$cycloalkylcarbonyl, thenoyl, furoyl, benzoyl or $C_1$-$C_{12}$alkyl-substituted benzoyl;

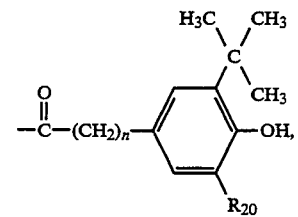

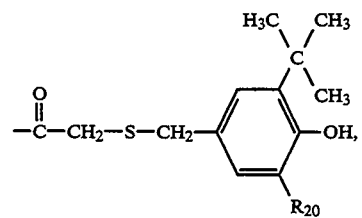

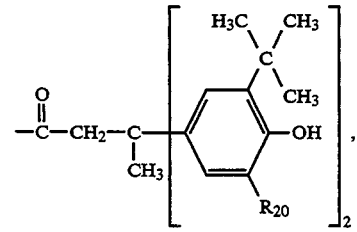

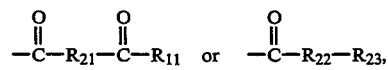

and,
when m is 2,
$R_1$ is

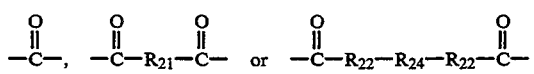

and,
m is 3,
$R_1$ is $C_4$-$C_{18}$alkanetricarbonyl, $C_9$-$C_{18}$aryltricarbonyl,

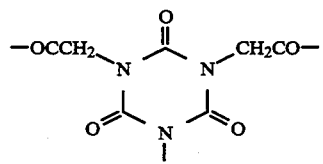

or

-continued

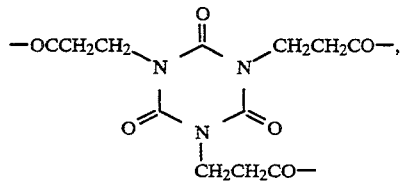

and, when m is 4, $R_1$ is $C_6$–$C_{18}$alkanetetracarbonyl or $C_{10}$–$C_{18}$aryltetracarbonyl, $R_2$, $R_3$, $R_4$ and $R_5$, independently of one another, are hydrogen, chlorine, $C_1$–$C_{25}$alkyl, $C_7$–$C_9$phenylalkyl, unsubstituted or $C_1$–$C_4$alkyl-substituted phenyl, unsubstituted or $C_1$–$C_4$-alkyl-substituted $C_5$–$C_8$cycloalkyl; $C_1$–$C_{18}$alkoxy, $C_1$–$C_{18}$alkylthio, hydroxyl, $C_1$–$C_4$alkylamino, di($C_1$–$C_4$alkyl)amino, $C_1$–$C_{25}$alkanoyloxy, $C_1$–$C_{25}$alkanoylamino, $C_3$–$C_{25}$alkenoyloxy, $C_3$–$C_{25}$alkanoyloxy which is interrupted by oxygen, sulfur or

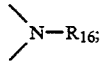

$C_6$–$C_9$cycloalkylcarbonyloxy, benzoyloxy or $C_1$–$C_2$alkyl-substituted benzoyloxy, or, furthermore, the radicals $R_2$ and $R_3$ or the radicals $R_3$ and $R_4$ or the radicals $R_4$ and $R_5$ together with the carbon atoms to which they are attached form a phenyl ring, $R_4$ is additionally —$(CH_2)_n$—$COR_{11}$, or, when $R_3$, $R_5$, $R_6$, $R_7$ and $R_{10}$ are hydrogen, $R_4$ is additionally a radical of the formula (2)

(2)

in which $R_1$ is as defined above for m=1,
$R_6$ is hydrogen or a radical of the formula (3)

(3)

in which $R_4$ is not a radical of the formula (2) and $R_1$ is as deemed above for m=1, $R_7$, $R_8$, $R_9$ and $R_{10}$, independently of one another, are hydrogen, $C_1$–$C_4$alkyl or $C_1$–$C_4$alkoxy, on the condition that at least one of the radicals $R_7$, $R_8$, $R_9$ and $R_{10}$ is hydrogen, $R_{11}$ is hydroxyl, $\left[ -O^{\ominus} \dfrac{1}{r} M^{r+} \right]$, $C_1$–$C_{18}$—Alkoxy or $-N\begin{smallmatrix}R_{14}\\ \\R_{15}\end{smallmatrix}$, $R_{12}$ and $R_{13}$, independently of one another, are hydrogen, $CF_3$, $C_1$–$C_{12}$alkyl or phenyl, or $R_{12}$ and $R_{13}$ together with the carbon atom to which they are attached form a $C_5$–$C_8$cycloalkylidene ring which is unsubstituted or substituted by 1 to 3 $C_1$–$C_4$alkyl groups;

$R_{14}$ and $R_{15}$ independently of one another, are hydrogen or $C_1$–$C_{18}$alkyl, $R_{16}$ is hydrogen or $C_1$–$C_8$alkyl, $R_{17}$ is hydrogen or $C_1$–$C_4$alkyl, $R_{18}$ is hydrogen, unsubstituted or $C_1$–$C_4$alkyl-substituted phenyl; $C_1$–$C_{25}$alkyl, $C_2$–$C_{25}$alkyl which is interrupted by oxygen, sulfur or

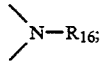

$C_7$–$C_9$phenylalkyl which is unsubstituted or substituted on the phenyl radical by 1 to 3 $C_1$–$C_4$alkyl groups; $C_7$–$C_{25}$phenylalkyl which is interrupted by oxygen, sulfur or

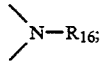

and unsubstituted or substituted on the phenyl radical by 1 to 3 $C_1$–$C_4$alkyl groups, or, furthermore, the radicals $R_{17}$ and $R_{18}$ together with the carbon atoms to which they are attached form a $C_5$–$C_{12}$cycloalkylene ring which is unsubstituted or substituted by 1 to 3 $C_1$–$C_4$alkyl groups; or, when $R_6$, $R_{17}$ and $R_{19}$ are hydrogen, $R_4$ is not a radical of the formula (2), m is 1 and $R_1$ is as defined above for m=1, $R_{18}$ is additionally a radical of the formula (4)

(4)

$R_{19}$ is hydrogen or $C_1$–$C_4$alkyl,
$R_{20}$ is hydrogen or $C_1$–$C_4$alkyl,
$R_{21}$ is a direct bond, $C_1$–$C_{18}$alkylene, $C_2$–$C_{18}$alkylene which is interrupted by oxygen, sulfur or

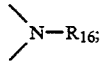

$C_2-C_{18}$alkenylene, $C_2-C_{20}$alkylidene, $C_7-C_{20}$phenylalkylidene, $C_5-C_8$-cycloalkylene, $C_7-C_8$-bicycloalkylene, unsubstituted or $C_1-C_4$alkyl-substituted phenylene,

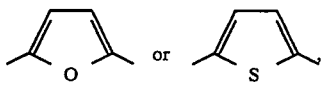

$R_{22}$ is oxygen, —NH— or

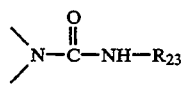

$R_{23}$ is $C_1-C_{18}$alkyl or phenyl,
$R_{24}$ is $C_2-C_{18}$alkylene, $C_5-C_8$cycloalkylene or phenylene,
$R_{25}$ is a direct bond, $C_1-C_{18}$alkylene or $C_2-C_{18}$alkylene which is interrupted by oxygen, sulfur or

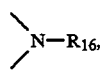

M is an r-valent metal cation,
m is 1, 2, 3 or 4, $R_6$ being hydrogen if m is 2, 3 or 4;
n is 0, 1 or 2 and
r is 1, 2 or 3.

2. A compound according to claim 1, in which, when m is 1,
$R_1$ is hydrogen, $C_1-C_{18}$alkanoyl, $C_3-C_{18}$alkenoyl, $C_3-C_{18}$alkanoyl which is interrupted by oxygen, sulfur or

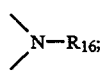

$C_2-C_{18}$alkanoyl which is substituted by a di($C_1-C_6$alkyl)-phosphonate group; $C_6-C_9$cycloalkylcarbonyl, thenoyl, furoyl, benzoyl or $C_1-C_8$alkyl-substituted benzoyl;

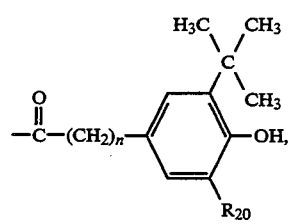

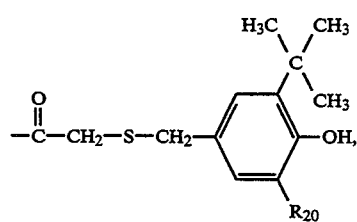

-continued

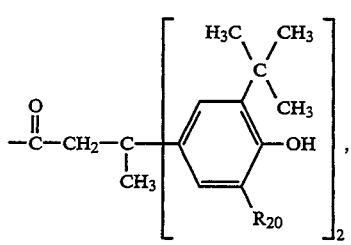

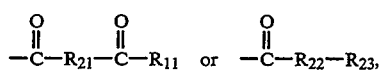

$R_2$, $R_3$, $R_4$ and $R_5$, independently of one another, are hydrogen, chlorine, $C_1-C_{18}$alkyl, benzyl, phenyl, $C_5-C_8$cycloalkyl, $C_1-C_{18}$alkoxy, $C_1-C_{18}$alkylthio, $C_1-C_{18}$alkanoyloxy, $C_1-C_{18}$alkanoylamino, $C_3-C_{18}$alkenoyloxy or benzoyloxy, or, furthermore, the radicals $R_2$ and $R_3$ or the radicals $R_4$ and $R_5$ together with the carbon atoms to which they are attached form a phenyl ring, or, when $R_3$, $R_5$, $R_6$, $R_7$ and $R_{10}$ are hydrogen, $R_4$ is additionally a radical of the formula (2), $R_7$, $R_8$, $R_9$ and $R_{10}$, independently of one another, are hydrogen or $C_1-C_4$alkyl, on the condition that at least one of the radicals $R_7$, $R_8$, $R_9$ and $R_{10}$ is hydrogen, $R_{12}$ and $R_{13}$ are methyl groups or together with the C atom to which they are attached form a $C_5-C_8$cycloalkylidene ring which is unsubstituted or substituted by 1 to 3 $C_1-C_4$alkyl groups, $R_{18}$ is hydrogen, phenyl, $C_1-C_8$alkyl, $C_2-C_{18}$alkyl which is interrupted by oxygen, sulfur

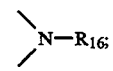

benzyl, $C_7-C_{18}$phenylalkyl which is interrupted by oxygen, sulfur or

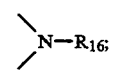

or, furthermore, the radicals $R_{17}$ and $R_{18}$ together with the carbon atoms to which they are attached form a $C_5-C_8$cycloalkylene ring which is unsubstituted or substituted by 1 to 3 $C_1-C_4$alkyl groups,
$R_{21}$ is a direct bond, $C_1-C_{12}$alkylene, $C_2-C_{12}$alkylene which is interrupted by oxygen, sulfur or

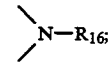

$C_2-C_{12}$alkenylene, $C_2-C_{12}$alkylidene, $C_7-C_{12}$phenylalkylidene, $C_5-C_8$-cycloalkylene $C_7-C_8$bicycloalkylene or phenylene,
$R_{24}$ is $C_2-C_{12}$alkylene, $C_5-C_8$cycloalkylene or phenylene, and
$R_{25}$ is a direct bond, $C_1-C_{12}$alkylene or $C_2-C_{12}$alkylene which is interrupted by oxygen, sulfuror

3. A compound according to claim 1, in which at least two of the radicals $R_2$, $R_3$, $R_4$ and $R_5$ are hydrogen.

4. A compound according to claim 1, in which $R_3$ and $R_5$ are hydrogen.

5. A compound according to claim 1, in which $R_2$, $R_3$, $R_4$ and $R_5$, independently of one another, are hydrogen, chlorine, $C_1$-$C_{18}$alkyl, $C_5$-$C_6$cycloalkyl or $C_1$-$C_4$alkoxy, or, furthermore, the radicals $R_2$ and $R_3$ together with the carbon atoms to which they are attached form a phenyl ring.

6. A compound according to claim 1, in which m is 1 or 2.

7. A compound according to claim 1, in which $R_{18}$ is hydrogen, $C_1$-$C_{12}$alkyl, $C_2$-$C_{12}$alkyl which is interrupted by oxygen or sulfur; $C_7$-$C_{12}$phenylalkyl which is interrupted by oxygen or sulfur, or, furthermore, the radicals $R_{17}$ and $R_{18}$ together with the carbon atoms to which they are attached form a $C_5$-$C_8$cycloalkylene ring.

8. A compound according to claim 1, in which, when m is 1, $R_1$ is hydrogen, $C_1$-$C_{18}$alkanoyl, $C_3$-$C_{12}$alkenoyl, $C_3$-$C_{12}$alkanoyl which is interrupted by oxygen; $C_2$-$C_{12}$alkanoyl which is substituted by a di($C_1$-$C_6$-alkyl)phosphonate group; $C_6$-$C_9$cycloalkycarbonyl, benzoyl,

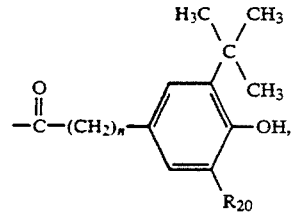

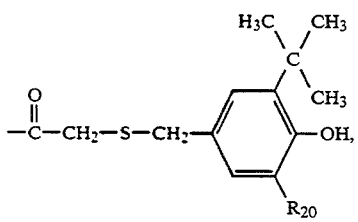

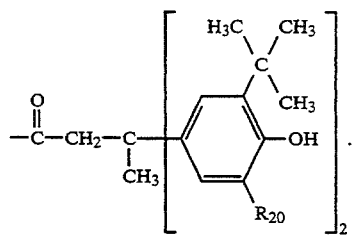

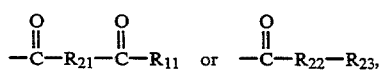

$R_2$, $R_3$, $R_4$ and $R_5$ independently of one another, are hydrogen, $C_1$-$C_{18}$alkyl, $C_5$-$C_7$cycloalkyl, $C_1$-$C_{12}$alkoxy, $C_1$-$C_{12}$alkanoyloxy or benzoyloxy, or, furthermore, the radicals $R_2$ and $R_3$ together with the carbon atoms to which they are attached form a phenyl ring, or, when $R_3$, $R_5$, $R_6$, $R_7$ and $R_{10}$ are hydrogen, $R_4$ is additionally a radical of the formula (2), $R_{12}$ and $R_{13}$ are methyl groups or together with the C atom to which they are attached form a $C_5$-$C_8$cycloalkylidene ring, $R_{18}$ is hydrogen, $C_1$-$C_{12}$alkyl, $C_2$-$C_{12}$alkyl which is interrupted by oxygen or sulfur; $C_7$-$C_{12}$phenylalkyl which is interrupted by oxygen or sulfur, or, furthermore, the radicals $R_{17}$ and $R_{18}$ together with the carbon atoms to which they are attached form a $C_5$-$C_8$cycloalkylene ring, $R_{21}$ is $C_1$-$C_{12}$alkylene, phenylene or $C_2$-$C_{12}$alkylene which is interrupted by oxygen or sulfur, $R_{23}$ is $C_1$-$C_2$alkyl, $R_{24}$ is $C_2$-$C_{12}$alkylene, or phenylene, $R_{25}$ is $C_1$-$C_8$alkylene or $C_2$-$C_8$alkylene which is interrupted by oxygen, and m is 1, 2 or 3.

9. A compound according to claim 1, in which, when m is 1, $R_1$ is hydrogen, $C_1$-$C_{18}$alkanoyl, $C_3$-$C_4$alkenoyl, $C_2$-$C_4$alkanoyl which is substituted by a di($C_1$-$C_4$alkyl)phosphonate group; cyclohexylcarbonyl, benzoyl,

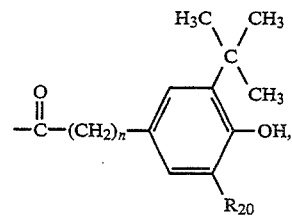

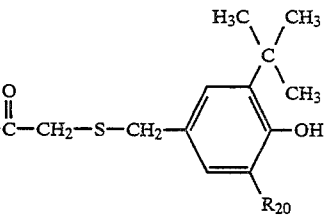

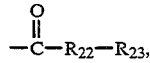

when m is 2, $R_1$ is

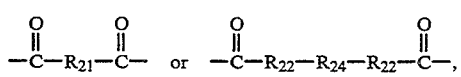

$R_2$ is hydrogen, $C_1$-$C_{18}$alkyl or cyclohexyl, $R_3$ is hydrogen, or, furthermore, the radicals $R_2$ and $R_3$ together with the carbon atoms to which they are attached form a phenyl ring, $R_4$ is $C_1$14 $C_4$alkyl or cyclohexyl, or, when $R_3$, $R_5$, $R_6$, $R_7$ and $R_{10}$ are hydrogen, $R_4$ is additional a radical of the formula (2), in which $R_1$ is as defined above for m=1, $R_5$ is hydrogen, $R_6$ is hydrogen or a radical of the formula (3), in which $R_4$ is not a radical of the formula (2) and $R_1$ being as defined above for m=1, $R_7$ is hydrogen, $R_8$ and $R_9$, independently of one another, are hydrogen, $C_1$–$C_4$alkyl or $C_1$–$C_4$alkoxy, $R_{10}$ is hydrogen, $R_{12}$ and $R_{13}$ are methyl groups or, together with the C atom to which they are attached, form a cyclohexylidene ring, $R_{17}$ is hydrogen, $R_{18}$ is hydrogen, $C_1$–$C_4$alkyl, $C_2$–$C_8$alkyl which is interrupted by oxygen; or $C_7$–$C_9$phenylalkyl which is interrupted by oxygen, or, furthermore, the radicals $R_{17}$ and $R_{18}$ together with the carbon atoms to which they are attached form a cyclohexylene ring, $R_{19}$ is hydrogen, $R_{20}$ is hydrogen or $C_1$–$C_4$alkyl, $R_{21}$ is $C_1$–$C_8$alkylene, $C_2$–$C_6$alkylene which is interrupted by sulfur; or phenylene, $R_{22}$ is —NH— or

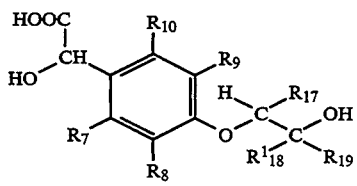

$R_{23}$ is $C_1$–$C_4$alkyl, $R_{24}$ is $C_4$–$C_8$alkylene, m is 1 or 2, and n is 0 or 2.

10. A compound of the formula (9)

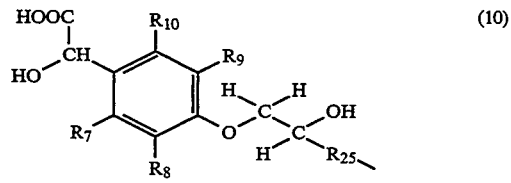

(9)

in which $R_7$, $R_8$, $R_9$ and $R_{10}$, independently of one another, are hydrogen, $C_1$–$C_4$alkyl or $C_1$–$C_4$alkoxy, on the condition that at least one of the radicals $R_7$, $R_8$, $R_9$ and $R_{10}$ is hydrogen and, when $R_7$, $R_8$, $R_9$ and $R_{10}$ are simultaneously hydrogen, either $R_{17}$, $R_{18}$ or $R_{19}$ is different from hydrogen, $R_{16}$ is hydrogen or $C_1$–$C_8$alkyl, $R_{17}$ is hydrogen or $C_1$–$C_4$alkyl, $R_{18}$ is hydrogen, unsubstituted or $C_1$–$C_4$alkyl-substituted phenyl; $C_2$–$C_{25}$alkyl, $C_2$–$C_{25}$alkyl which is interrupted by oxygen or sulfur; $C_7$–$C_9$phenylalkyl which is unsubstituted or substituted on the phenyl ring by 1 to 3 $C_1$–$C_4$alkyl groups; $C_7$–$C_{25}$phenylalkyl which is interrupted by oxygen, sulfur or

and unsubstituted or substituted on the phenyl ring by 1 to 3 $C_1$–$C_4$alkyl groups, or, furthermore, the radicals $R_{17}$ and $R_{18}$ together with the carbon atoms to which they are attached form a $C_5$–$C_{12}$cycloalkylene ring which is unsubstituted or substituted by 1 to 3 $C_3$–$C_4$alkyl groups; or, when $R_{17}$ and $R_{19}$ are hydrogen, $R_{18}^1$ is additionally a radical of the formula (10)

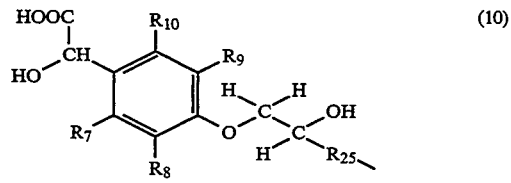

(10)

$R_{19}$ is hydrogen or $C_1$–$C_4$alkyl, and $R_{25}$ is a direct bond, $C_1$–$C_{18}$alkylene or $C_2$–$C_{18}$alkylene which is interrupted by oxygen, sulfur or

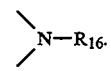

11. A compound according to claim 10, in which $R_{18}$ is hydrogen, phenyl, $C_1$–$C_{18}$alkyl, $C_2$–$C_{18}$alkyl which is interrupted by oxygen or sulfur; benzyl, $C_7$–$C_{18}$phenylalkyl which is interrupted by oxygen, sulfur or

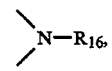

or, furthermore, the radicals $R_{17}$ and $R_{18}^1$ together with the carbon atoms to which they are attached form a $C_5$–$C_8$cycloalkylene ring which is unsubstituted or substituted by 1 to 3 $C_1$–$C_4$alkyl groups, and $R_{25}$ is a direct bond, $C_1$–$C_{12}$alkylene or $C_2$–$C_{12}$alkylene which is interrupted by oxygen, sulfur or

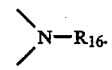

12. A compound according to claim 10, in which $R_7$ and $R_{10}$ are hydrogen.

13. A compound according to claim 10, in which $R_{17}$ is hydrogen, $R_{18}^1$ is hydrogen, $C_1$–$C_{12}$alkyl, $C_2$–$C_{12}$alkyl which is interrupted by oxygen or sulfur;

$C_7$–$C_{12}$phenylalkyl which is interrupted by oxygen or sulfur, or, furthermore, the radicals $R_{17}$ and $R_{18}$ together with the carbon atoms to which they are attached form a $C_5$–$C_8$-cycloalkylene ring, and $R_{25}$ is $C_1$–$C_8$alkylene or $C_2$–$C_8$alkylene which is interrupted by oxygen.

14. A compound according to claim 10, in which $R_7$, $R_{10}$, $R_{17}$ and $R_{19}$ are hydrogen, and $R_{18}^1$ is hydrogen, $C_1$–$C_4$alkyl, $C_2$–$C_8$alkyl which is interrupted by oxygen; $C_7$–$C_9$phenylalkyl which is interrupted by oxygen, or, furthermore, the radicals $R_{17}$ and $R_{18}$ together with the carbon atoms to which they are attached form a cyclohexylene ring.

* * * * *